United States Patent
Kim et al.

(10) Patent No.: US 11,028,428 B2
(45) Date of Patent: Jun. 8, 2021

(54) PEPTIDE NUCLEIC ACID PROBE FOR MULTIPLEX DETECTION OF BCR/ABL NEGATIVE MYELOPROLIFERATIVE NEOPLASM-ASSOCIATED GENE MUTATIONS

(71) Applicant: THE CATHOLIC UNIVERSITY OF KOREA INDUSTRY-ACADEMIC COOPERATION FOUNDATION, Seoul (KR)

(72) Inventors: Yonggoo Kim, Seoul (KR); Myungshin Kim, Seoul (KR); Joonhong Park, Daejeon (KR); Minsik Song, Daejeon (KR); Heekyung Park, Daejeon (KR); KyungTak Kim, Daejeon (KR)

(73) Assignee: THE CATHOLIC UNIVERSITY OF KOREA INDUSTRY-ACADEMIC COOPERATION FOUNDATION, Seoul (KR)

(*) Notice: Subject to any disclaimer, the term of this patent is extended or adjusted under 35 U.S.C. 154(b) by 193 days.

(21) Appl. No.: 15/775,591

(22) PCT Filed: Jun. 3, 2016

(86) PCT No.: PCT/KR2016/005927
§ 371 (c)(1),
(2) Date: May 11, 2018

(87) PCT Pub. No.: WO2017/082503
PCT Pub. Date: May 18, 2017

(65) Prior Publication Data
US 2018/0355414 A1    Dec. 13, 2018

(30) Foreign Application Priority Data
Nov. 11, 2015 (KR) .................... 10-2015-0158056

(51) Int. Cl.
*C12Q 1/68* (2018.01)
*C12Q 1/6827* (2018.01)
*C12Q 1/6886* (2018.01)

(52) U.S. Cl.
CPC ......... *C12Q 1/6827* (2013.01); *C12Q 1/6886* (2013.01); *C12Q 2600/156* (2013.01)

(58) Field of Classification Search
None
See application file for complete search history.

(56) References Cited

FOREIGN PATENT DOCUMENTS

| | | |
|---|---|---|
| CN | 1932038 A | 3/2007 |
| JP | 2015070808 A | 4/2015 |
| KR | 20120068992 A | 6/2012 |
| KR | 10-2014-0091944 A | 7/2014 |
| WO | 2015/036599 A1 | 3/2015 |

OTHER PUBLICATIONS

Seitz (Angew. Chem. Int. Ed. 2000, vol. 39, pp. 3249-3252).*
Kim, Bo Hyun et al., "JAK2V617F, MPL, CALR Mutations in Korean Patients with Essential Thrombocythemia and Primary Myelofibrosis," Journal of Korean Medical Science, vol. 30, pp. 882-888, 2015.

* cited by examiner

*Primary Examiner* — Jehanne S Sitton
(74) *Attorney, Agent, or Firm* — Sughrue Mion, PLLC

(57) ABSTRACT

The present invention provides a peptide nucleic acid probe including any one or more selected from the group consisting of nucleic acid sequences represented by SEQ ID NOs: 7-10 and nucleic acid sequences complementary to the nucleic acid sequences, and manufactured so as to complementarily bind to a BCR/ABL negative myeloproliferative neoplasm-associated gene, thereby enabling multiplex detection of gene mutations; a composition for multiplex detection of gene mutations comprising the same; a kit; and a method for multiplex detection of BCR/ABL negative myeloproliferative neoplasm-associated gene mutations using the same. Therefore, since multiplex detection of BCR/ABL negative myeloproliferative neoplasm-associated gene mutations can be rapidly and accurately carried out by one detection process, BCR/ABL negative myeloproliferative neoplasm is effectively diagnosed, and thus the present invention can be useful for diagnosis, follow-up, prognosis estimation, and treatment of diseases.

4 Claims, 26 Drawing Sheets

Specification includes a Sequence Listing.

[FIG. 1]

```
                              JAK2m-F
JAK2_WT       TCTTCTTGAAGCAGCAAGTATGATGAGCAAGCTTTCTCACAAGCATTTGGTTTTAAAT  60
JAK2_V617F1   TCTTCTTGAAGCAGCAAGTATGATGAGCAAGCTTTCTCACAAGCATTTGGTTTTAAAT  60
JAK2_V617F2   TCTTCTTGAAGCAGCAAGTATGATGAGCAAGCTTTCTCACAAGCATTTGGTTTTAAAT  60
              ************************************************************

JAK2-2                              JAK2m-R
JAK2_WT       TATGGAGTATGTGTCTGTGGAGACGAGAGTAAGTAAAACTACAGGCTTTCTAATGCCTTT  120
JAK2_V617F1   TATGGAGTATGTTTGTGTGGAGACGAGAGTAAGTAAAACTACAGGCTTTCTAATGCCTTT  120
JAK2_V617F2   TATGGAGTATGTTTTGTGGAGACGAGAGTAAGTAAAACTACAGGCTTTCTAATGCCTTT  120
              ************  *  *******************************************

JAK2_WT       CTCAGAGCATCTGTTTTGTTATATAGAAAATTCAGTTTCAGGATC  167  (SEQ ID NO:22)
JAK2_V617F1   CTCAGAGCATCTGTTTTGTTATATAGAAAATTCAGTTTCAGGATC  167  (SEQ ID NO:23)
JAK2_V617F2   CTCAGAGCATCTGTTTTGTTATATAGAAAATTCAGTTTCAGGATC  167  (SEQ ID NO:24)
              *********************************************
```

(SEQ ID NO:28)
(SEQ ID NO:29)
(SEQ ID NO:30)

[FIG. 4]
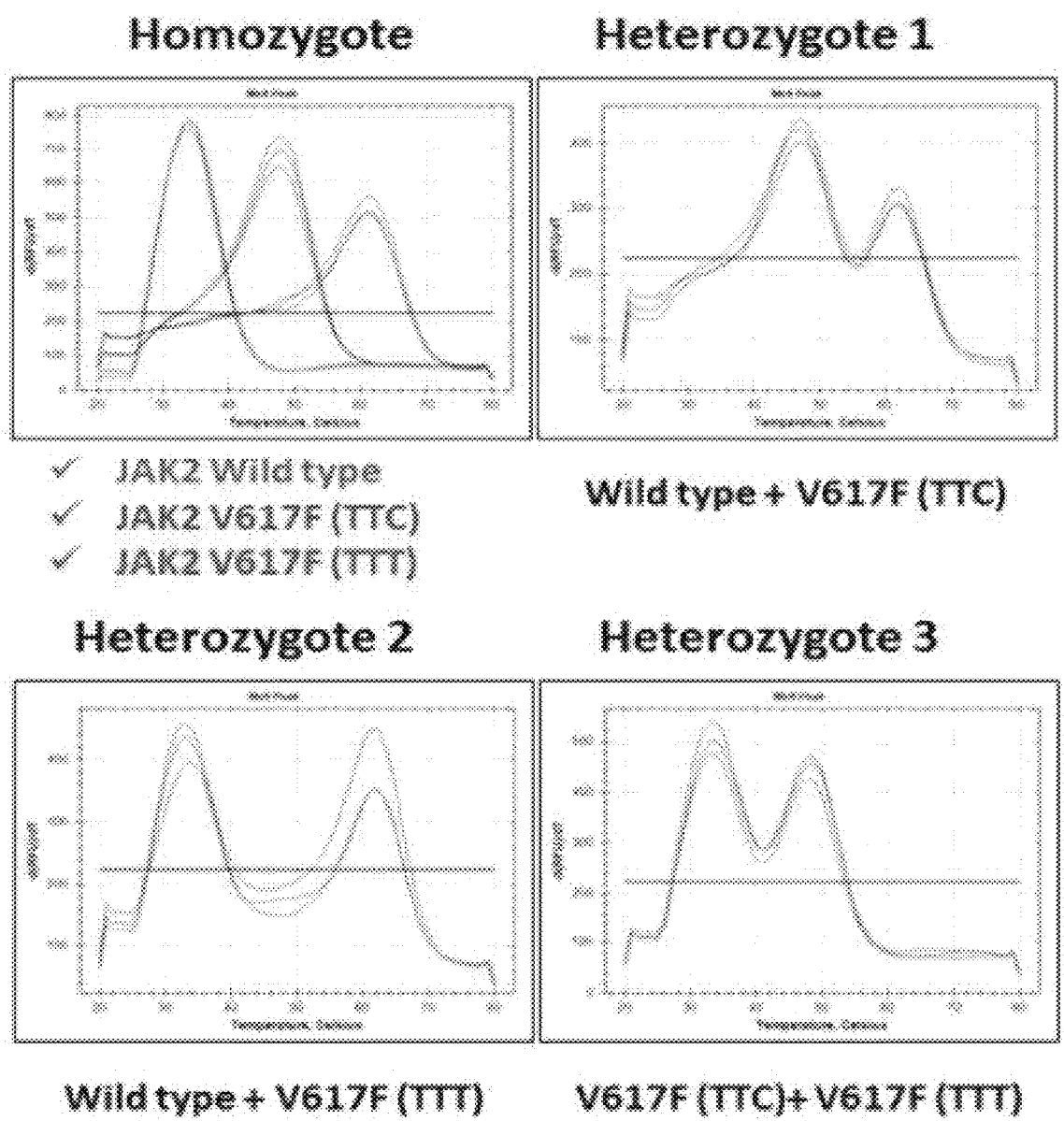

[FIG. 5]
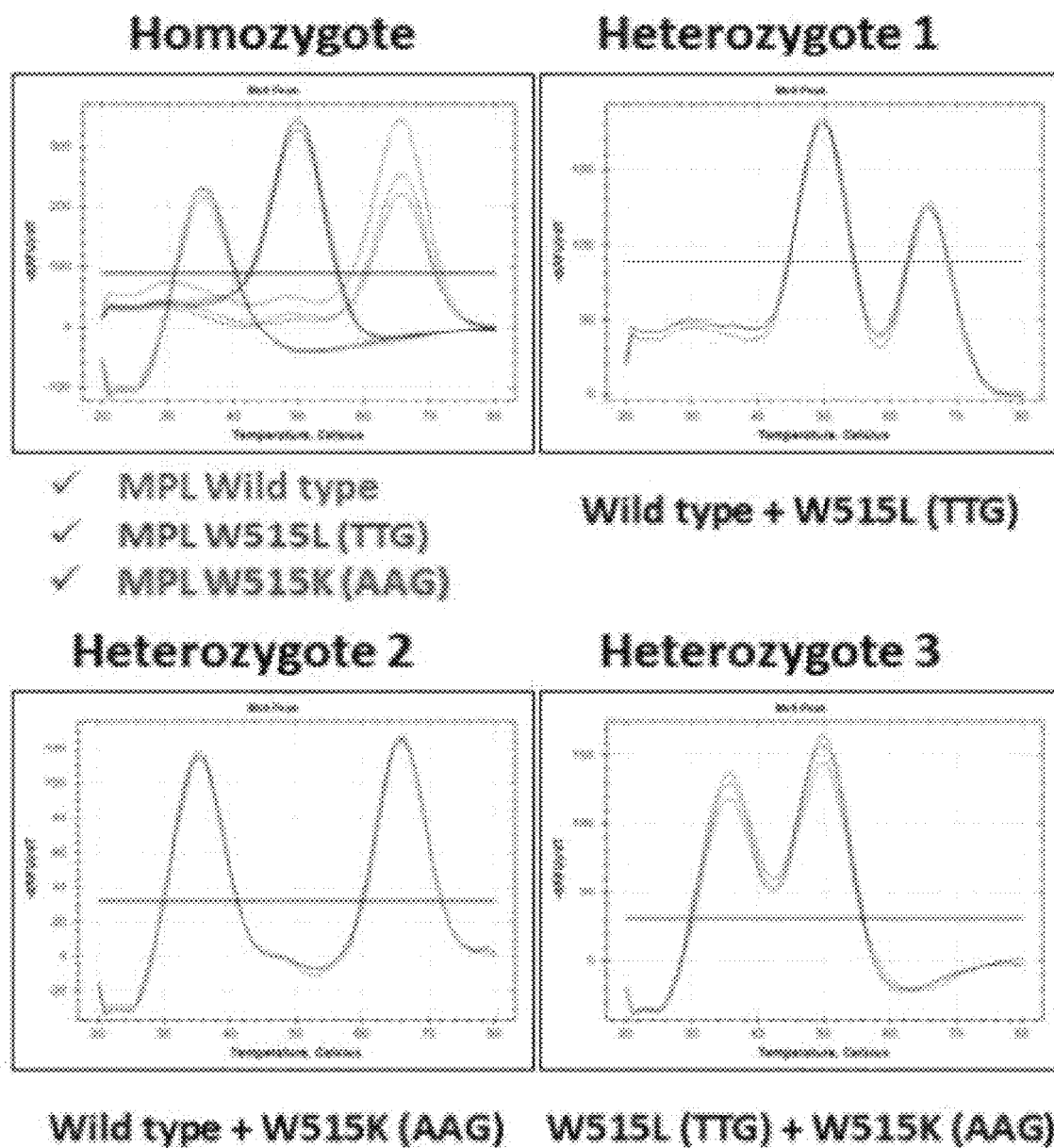

[FIG. 6]
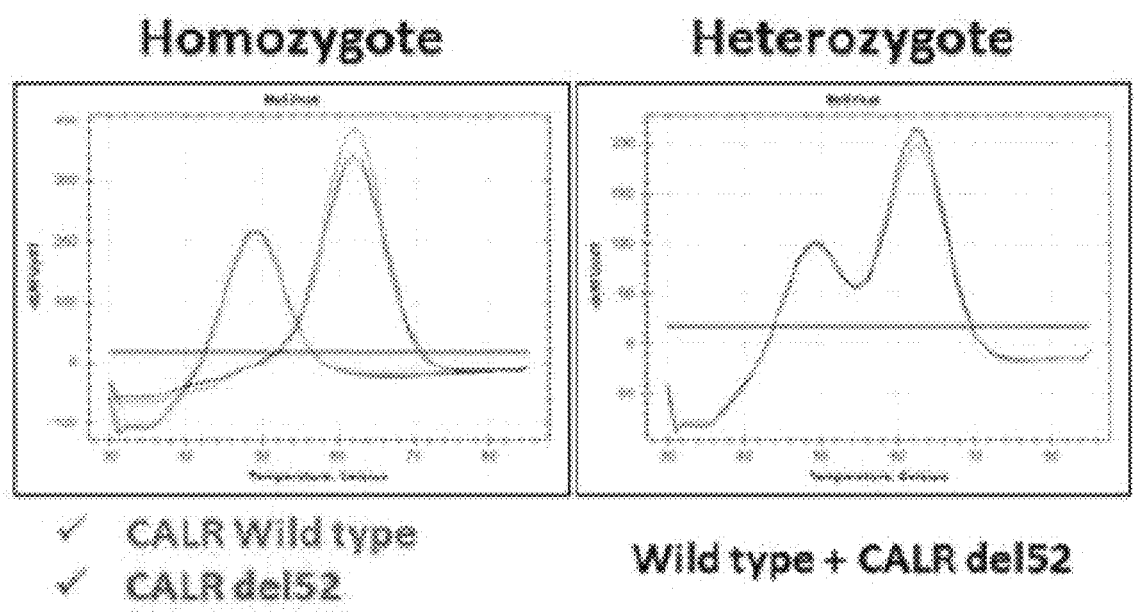

[FIG. 7]
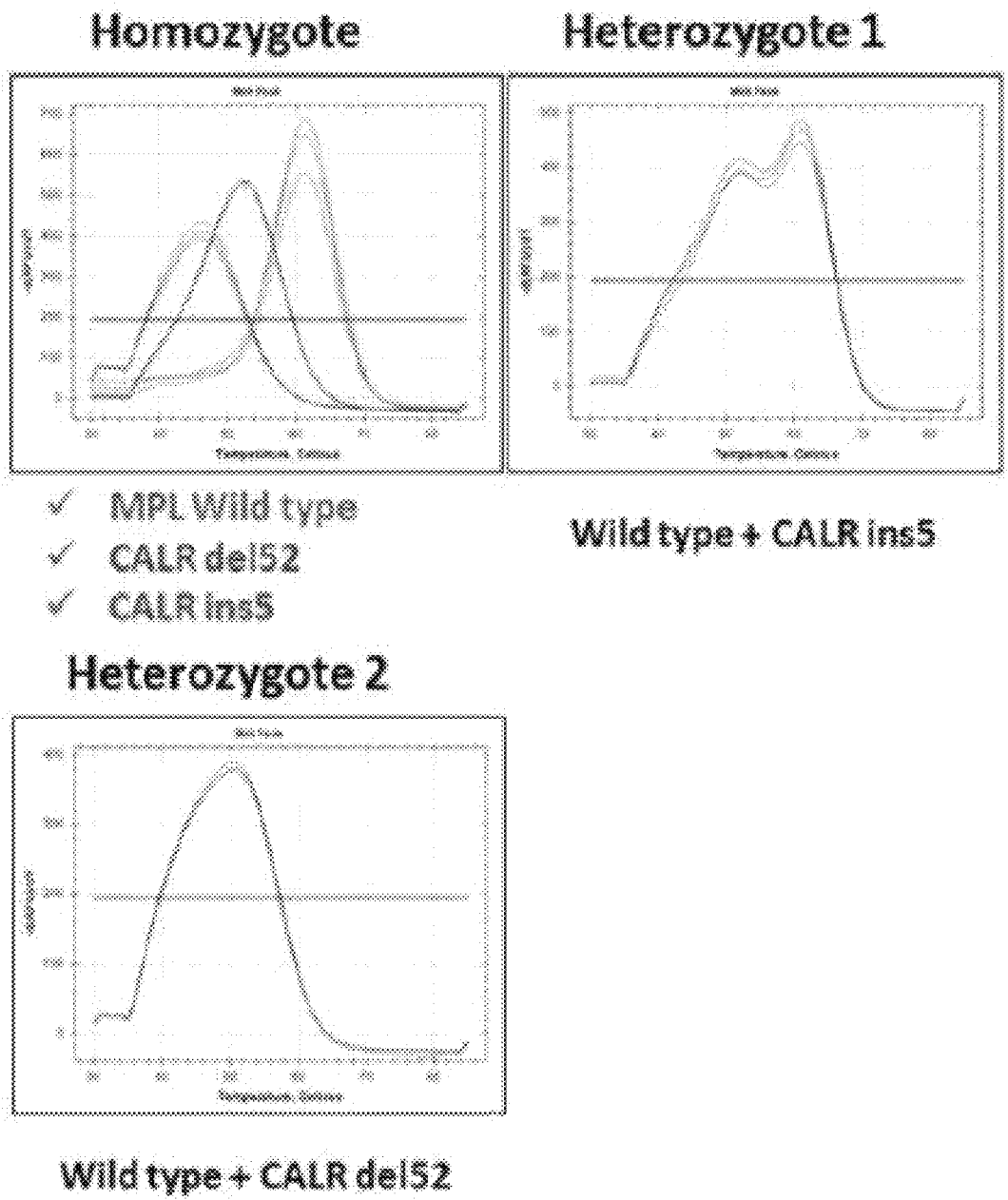

[FIG. 8]
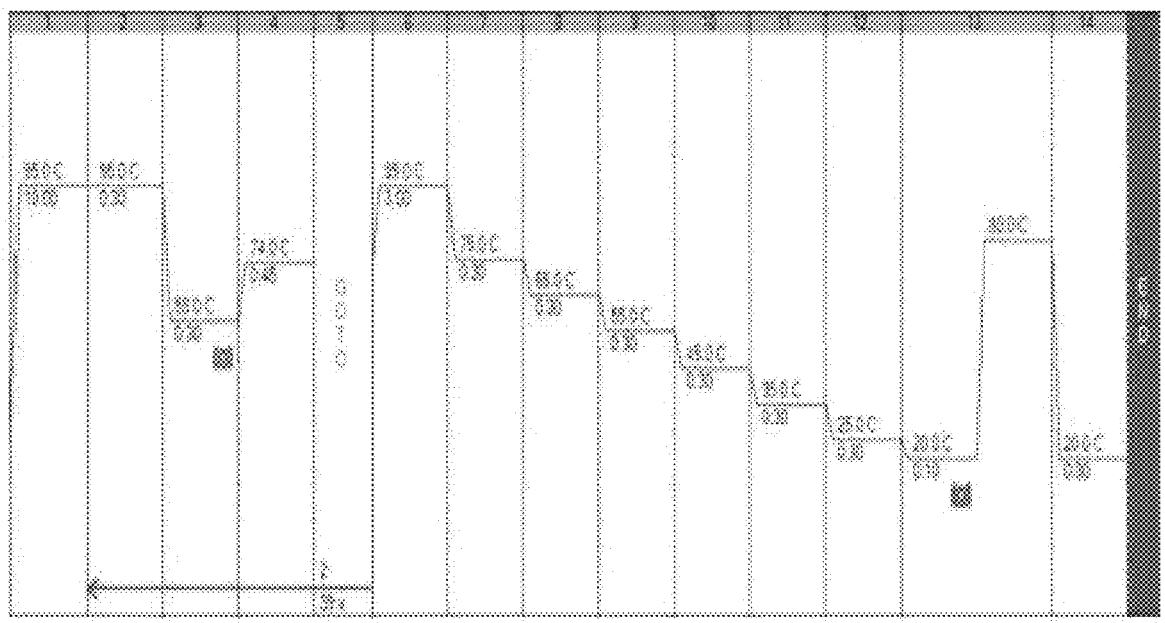

[FIG. 9]
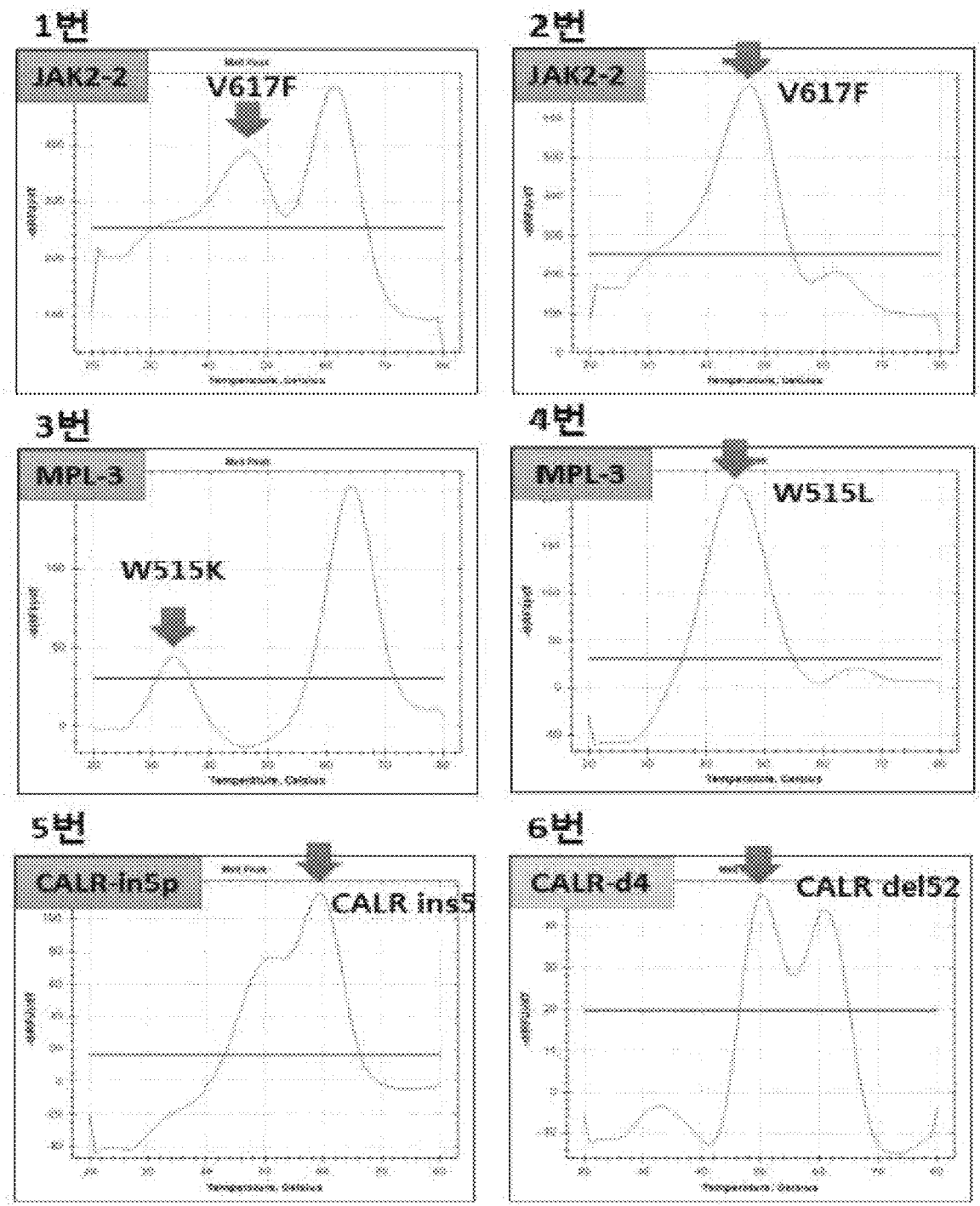

[FIG. 10]
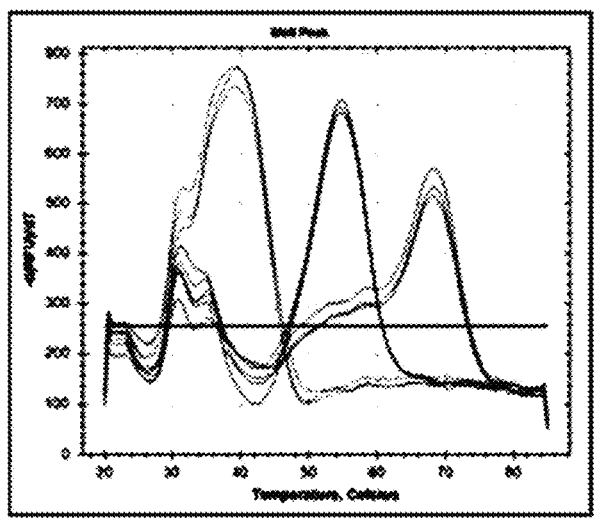
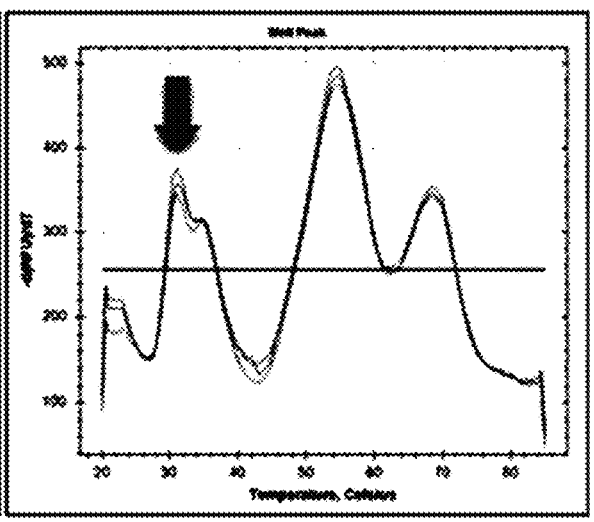
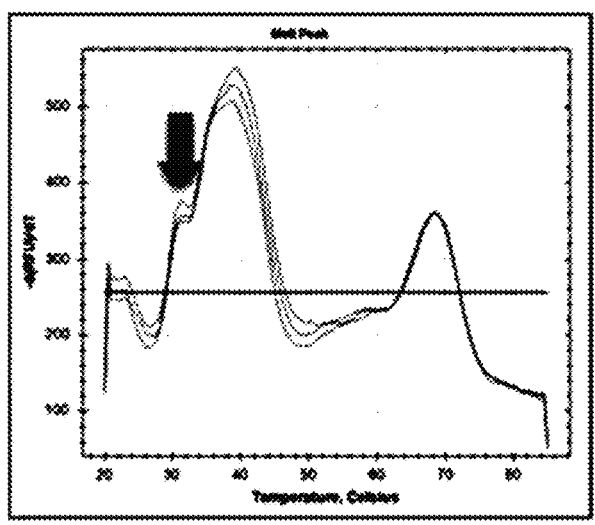
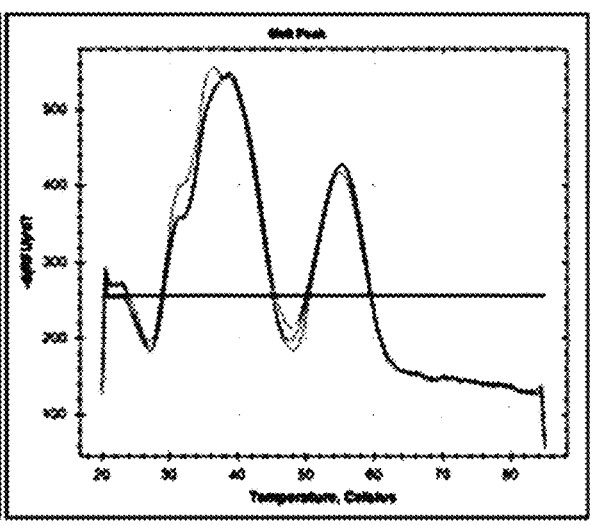

[FIG. 11]
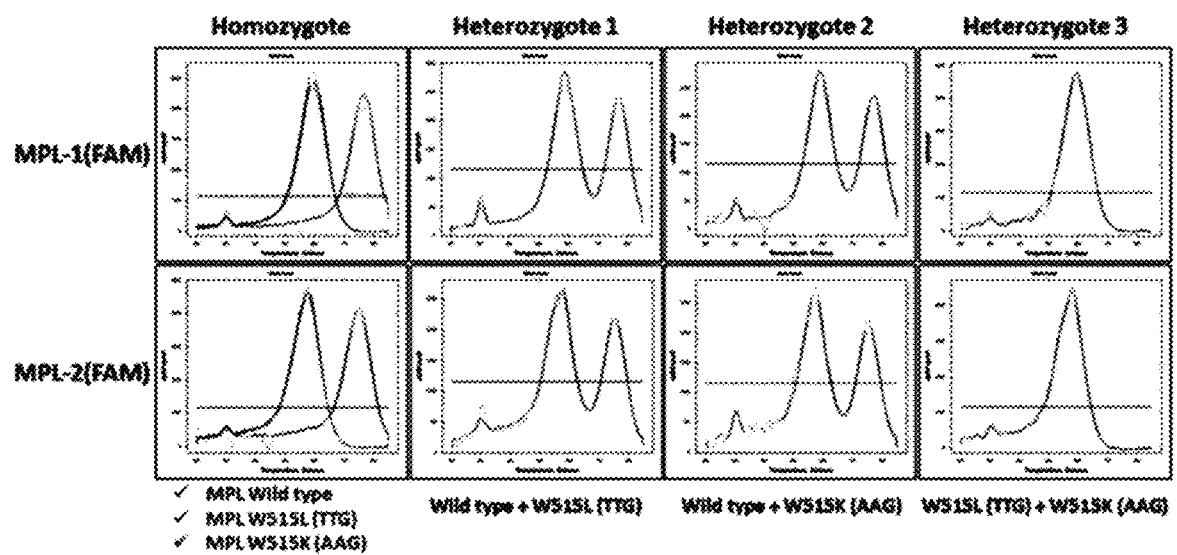

[FIG. 12]
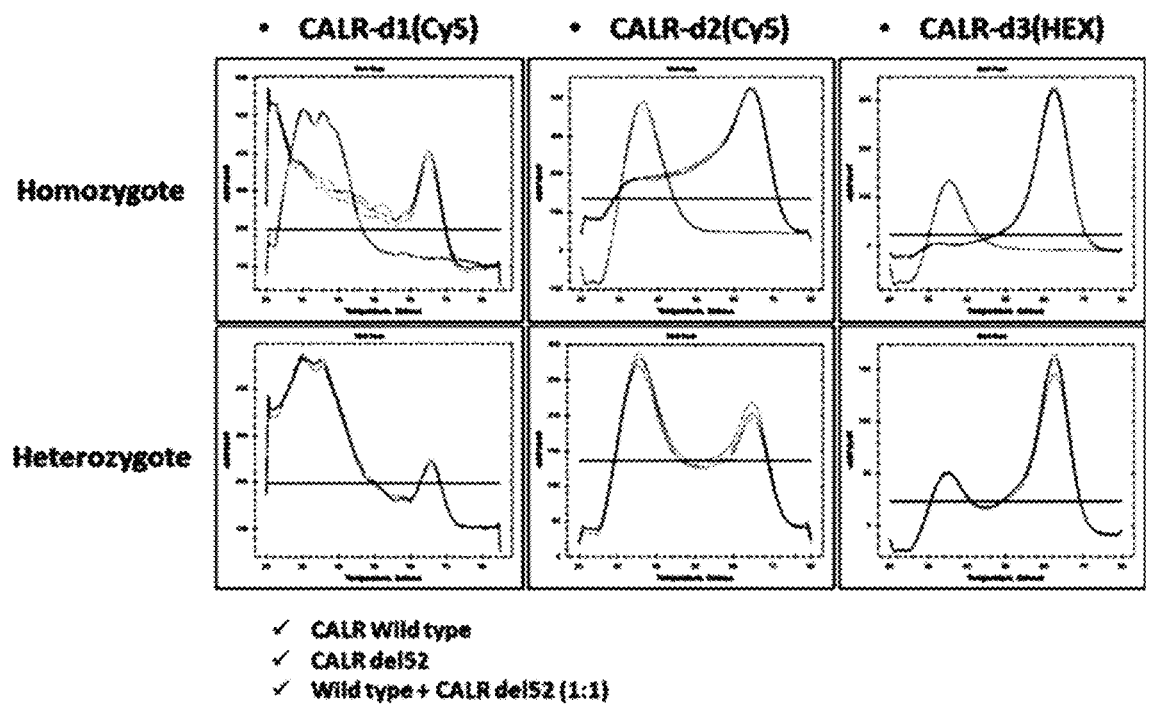

[FIG. 13]
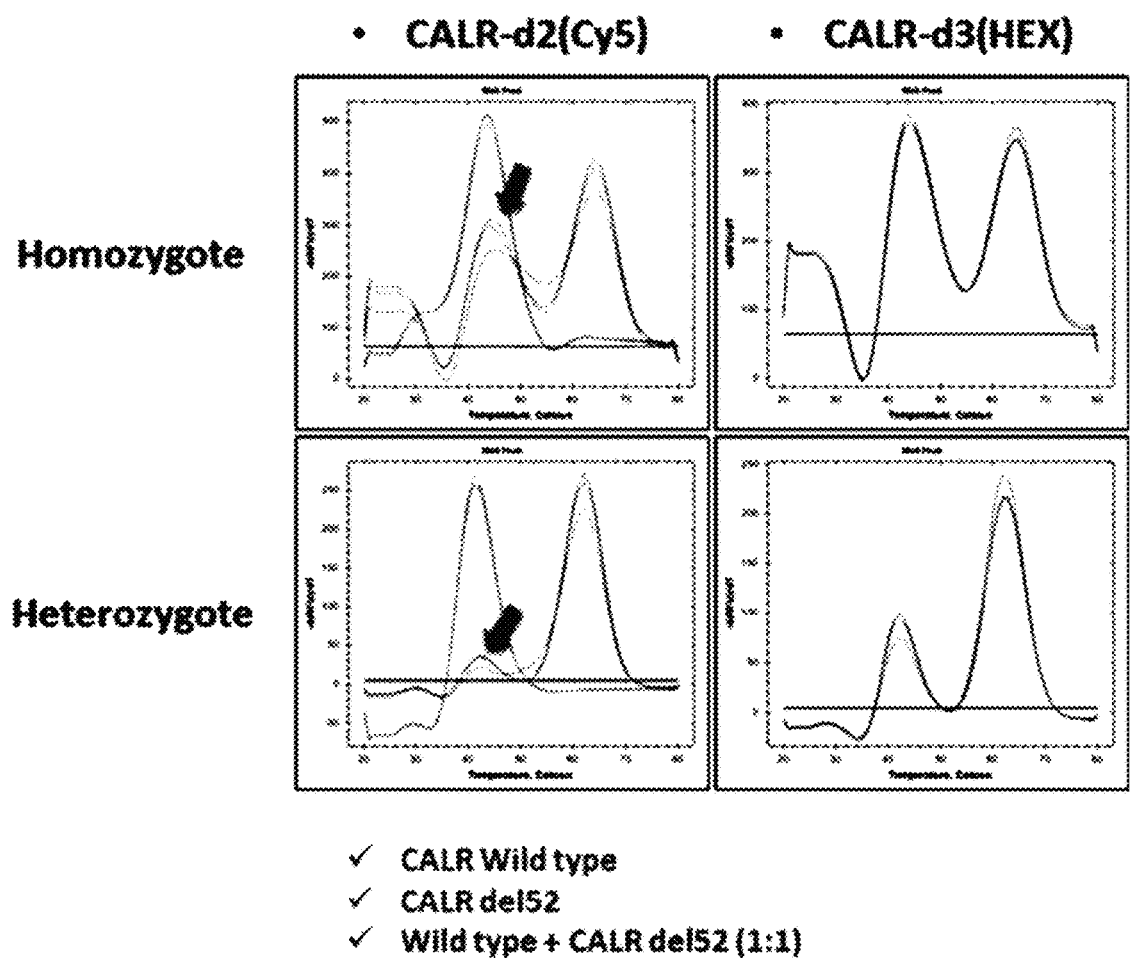

[FIG. 14]
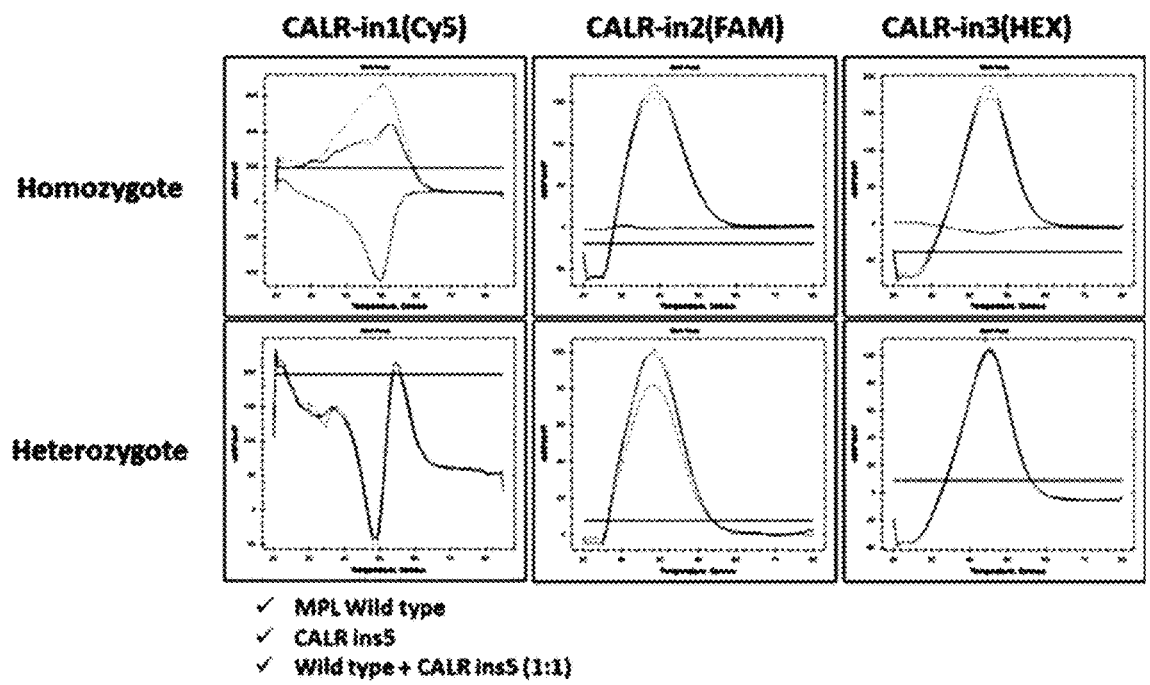

[FIG. 15a]
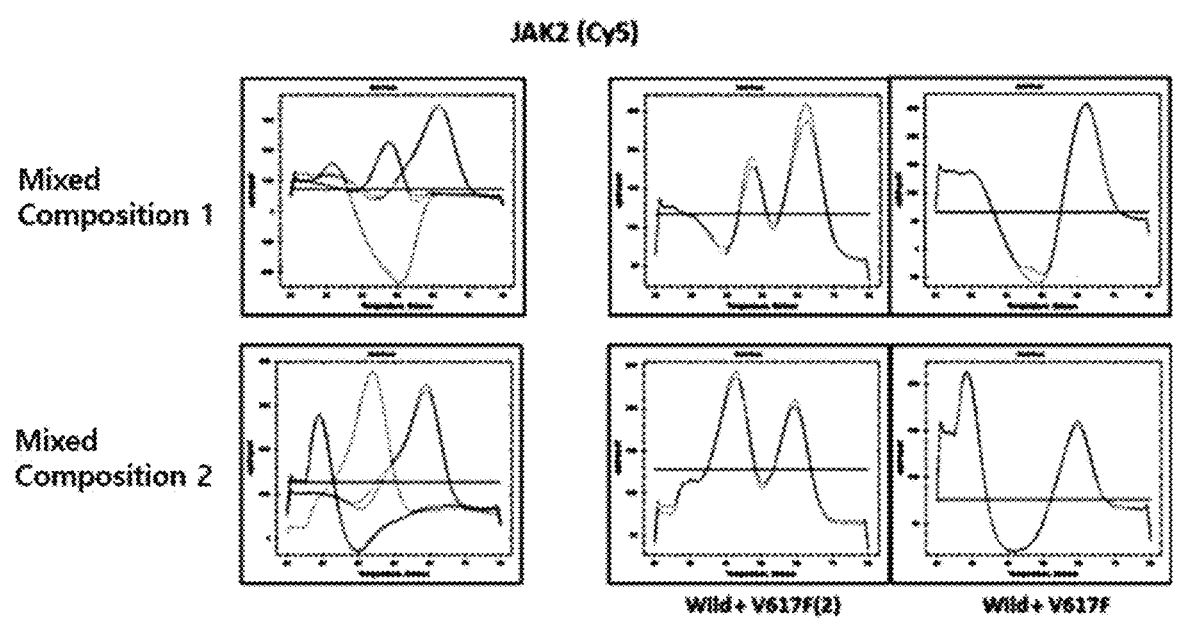

[FIG. 15b]
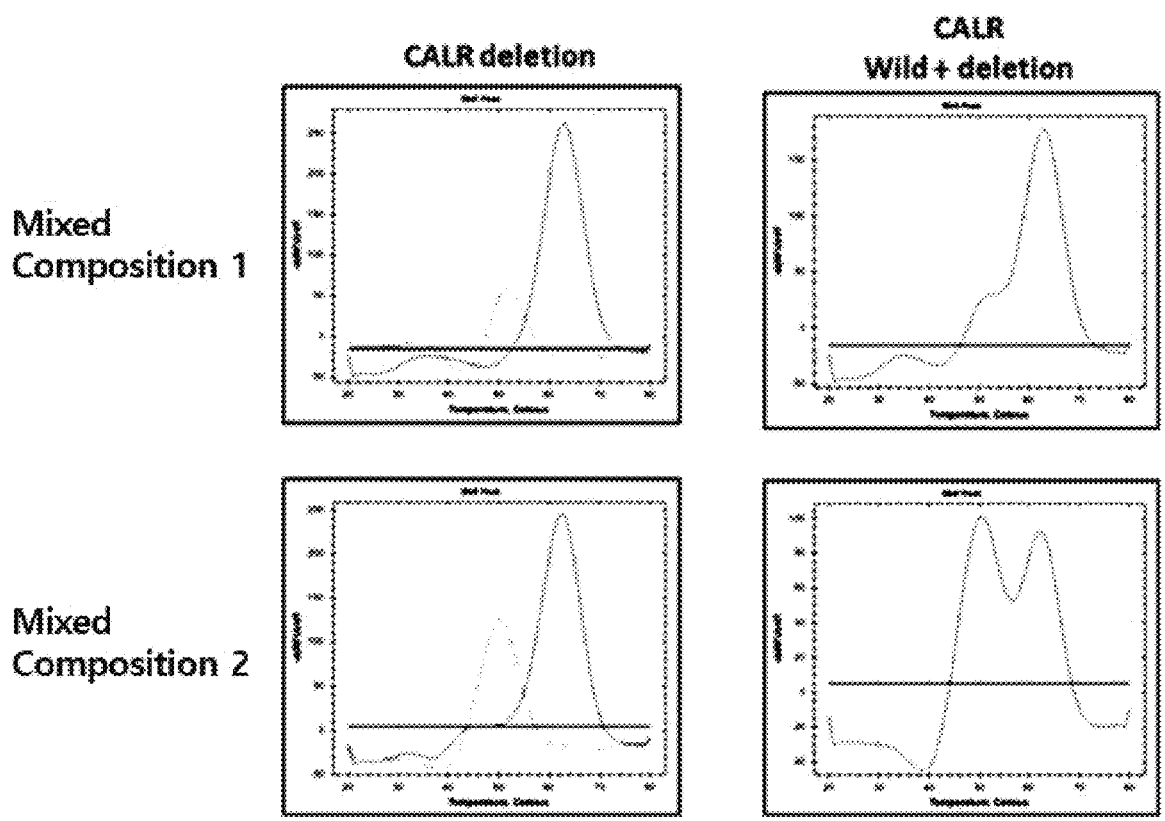

[FIG. 16a]
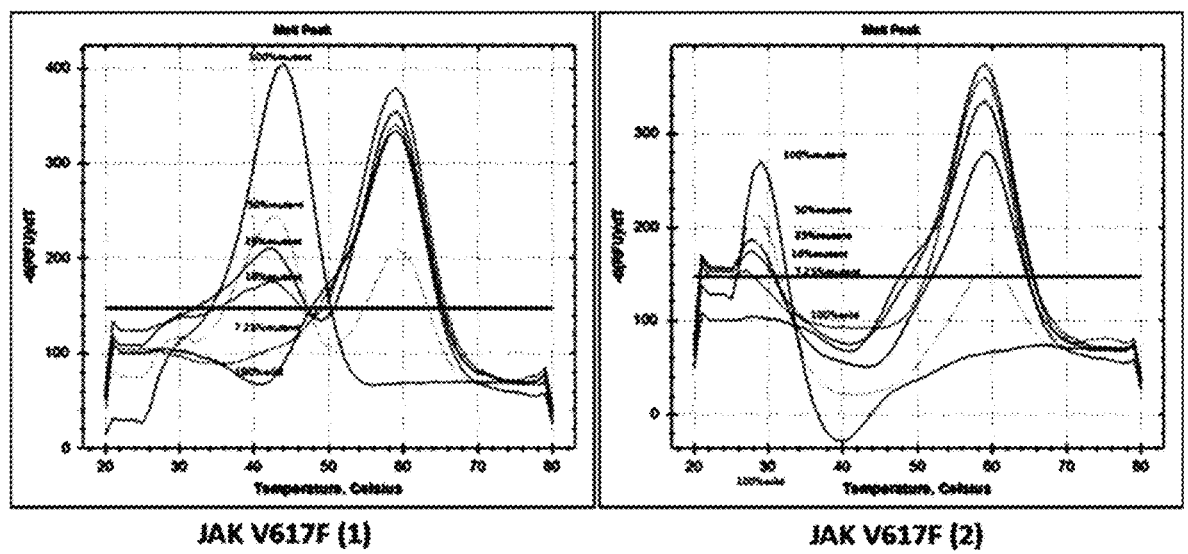

[FIG. 16b]
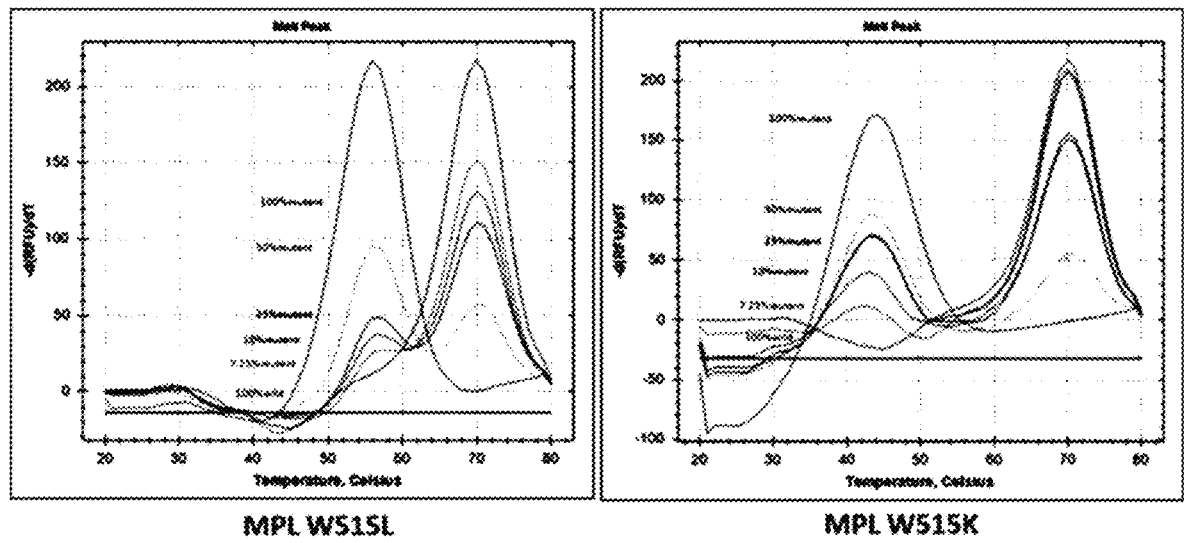

[FIG. 16c]
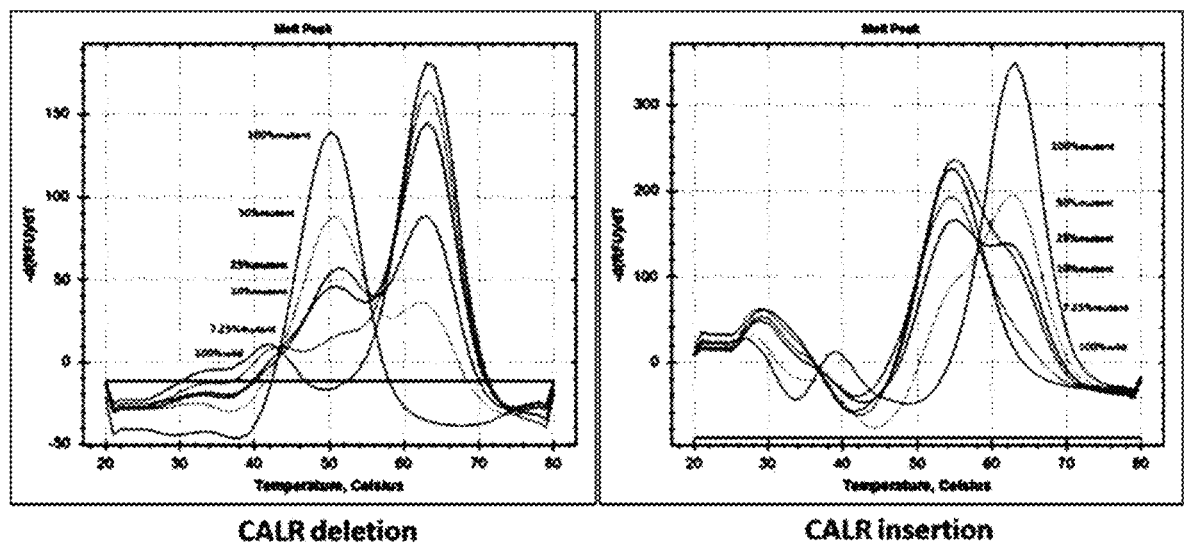

[FIG. 17]
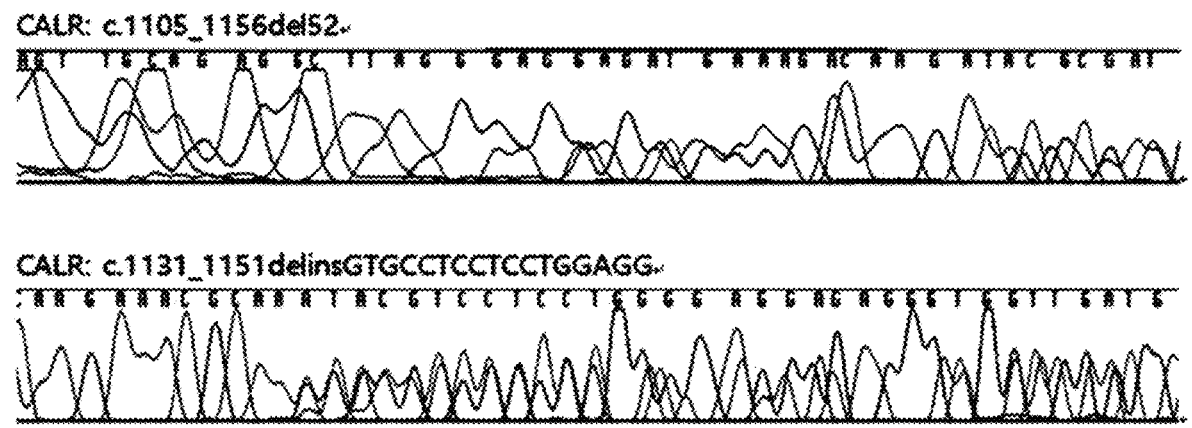

[FIG. 18]
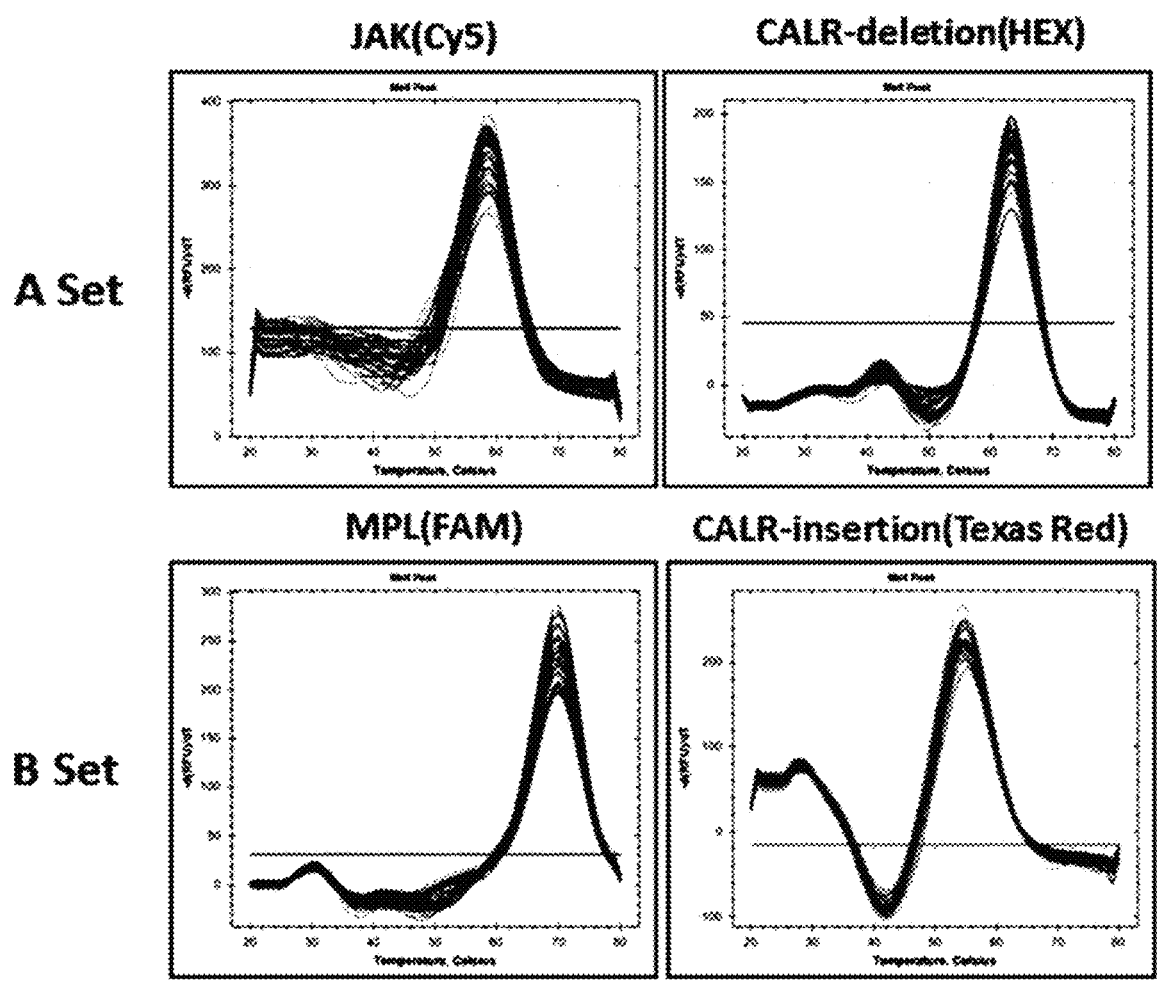

[FIG. 19]
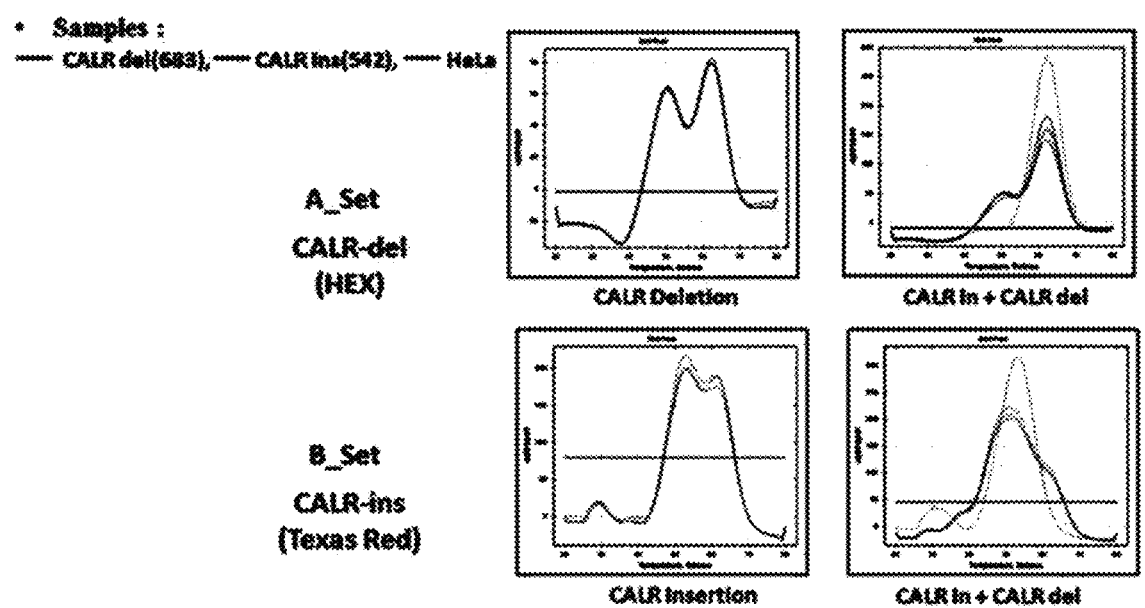

[FIG. 20a]
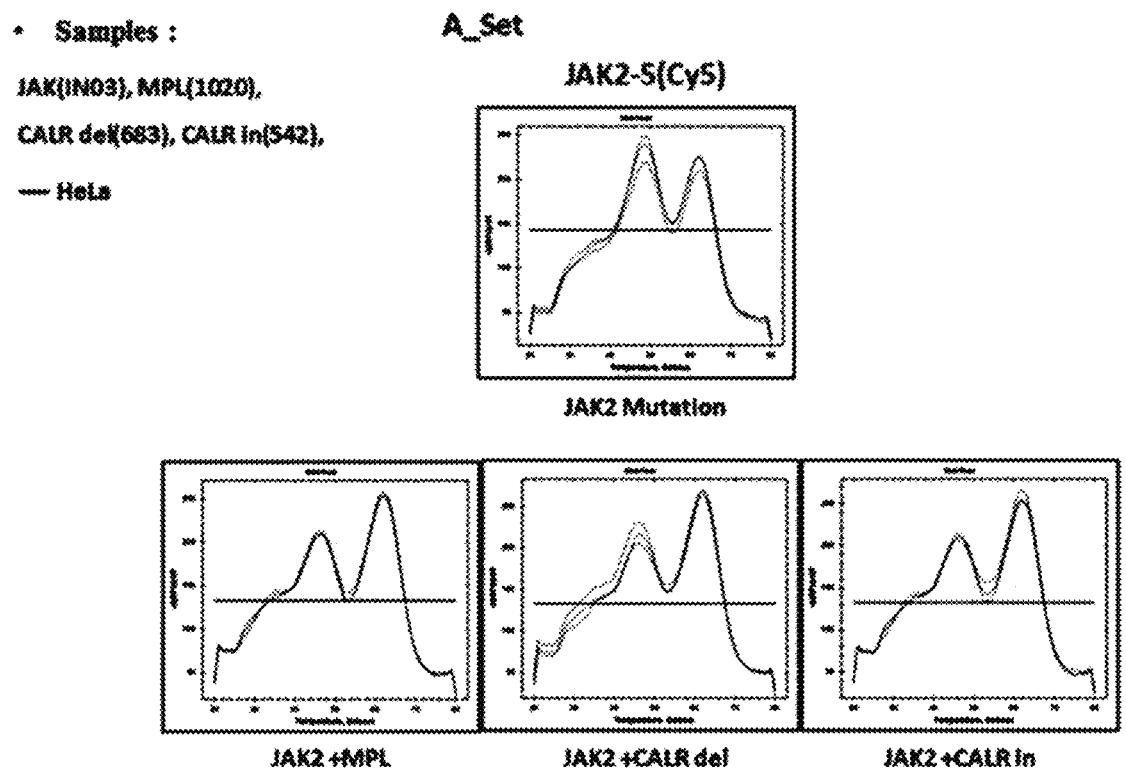

[FIG. 20b]
- Samples:
JAK(510), MPL(1020),
CALR del(683), CALR in(542),
— HeLa
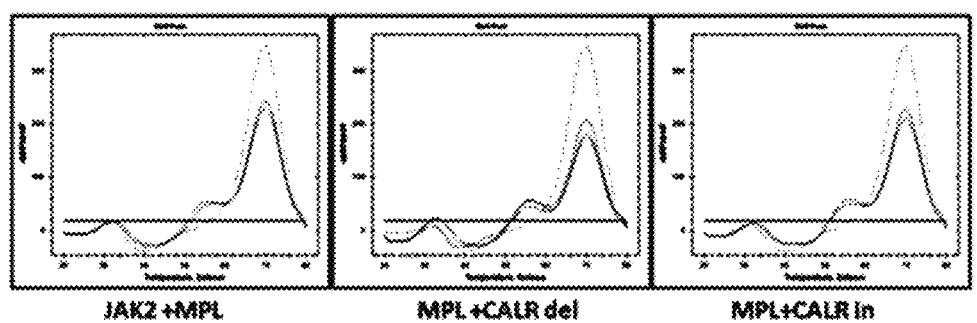

[FIG. 21a]
* Samples:  A_Set
JAK(610), MPL(1020),  CALR deletion(HEX)
CALR del(683), CALR in(542),
— HeLa
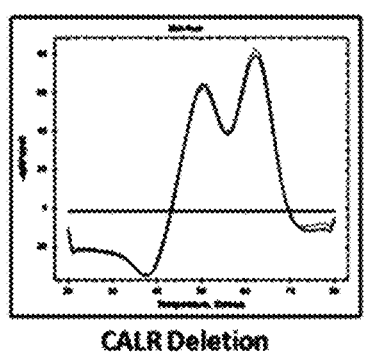
CALR Deletion
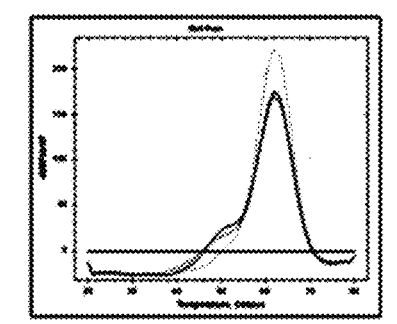
JAK2 + MPL + CALR in + CALR del

[FIG. 21b]
- Samples:
JAK(610), MPL(1020),
CALR del(683), CALR in(542),
— HeLa
B_Set
CALR insertion(TxR)
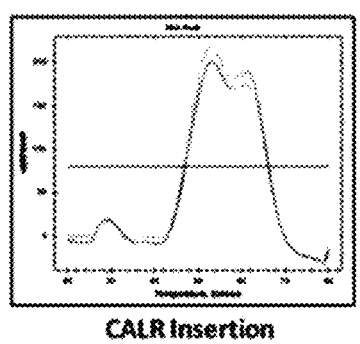
CALR Insertion
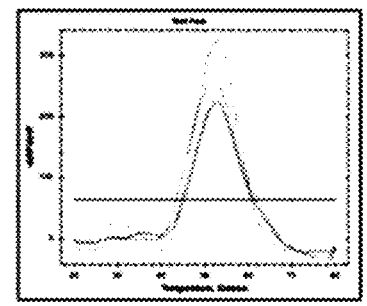
JAK2 + MPL + CALR in + CALR del

US 11,028,428 B2

PEPTIDE NUCLEIC ACID PROBE FOR MULTIPLEX DETECTION OF BCR/ABL NEGATIVE MYELOPROLIFERATIVE NEOPLASM-ASSOCIATED GENE MUTATIONS

CROSS REFERENCE TO RELATED APPLICATIONS AND CLAIM OF PRIORITY

This patent application is a National Phase application under 35 U.S.C. § 371 of International Application No. PCT/KR2016/005927, filed Jun. 3, 2016, which claims priority to Korean Patent Application No. 10-2015-0158056 filed Nov. 11, 2015, entire contents of which are incorporated herein by reference.

SEQUENCE LISTING

This application contains a Sequence Listing which is named Sequence Listing.txt.

BACKGROUND OF THE INVENTION

Technical Field of the Invention

The present invention relates to a peptide nucleic acid probe for multiplex detection of BCR/ABL negative myeloproliferative neoplasm-associated gene mutations, a composition for multiplex detection of gene mutations comprising the same, a multiplex detection kit, and a method for multiplex detection of gene mutations.

Description of the Related Art

Myeloproliferative neoplasm (MPN) is a clonal hematopoietic stem cell disease in which mature cells are overexpressed in one or more hemocyte lineages. According to 2008 WHO classification, myeloproliferative neoplasm includes BCR/ABL1 positive chronic myelogenous leukemia (CML), chronic neutrophilic leukemia, polycythaemia vera (PV), primary myelofibrosis (PMF), essential thrombocythaemia (ET), chronic eosinophilic leukemia (NOS), mastocytosis, unclassifiable myeloproliferative neoplasm, and the like.

Polycythaemia vera is myeloproliferative neoplasm characterized by increased erythropoiesis regardless of normal erythropoietic regulation, which results in panmyelosis that simultaneously proliferates not only red blood cell series but also granulocyte series, and megakaryocyte series. Polycythaemia vera is myeloproliferative neoplasm in which macrophages are proliferated primarily in which persistent thrombocytosis ($450 \times 10^9$/L or more) are shown in the peripheral blood, large and mature megakaryocytes increase in the bone marrow, and a long silent period is shown, but thrombosis or bleeding tendency may be shown. 30% of primary myelofibrosis patients are asymptomatic. Primary myelofibrosis is found incidentally by splenomegaly opinion, hematologic anemia, leukocytosis and platelet increases in blood tests. Leukoerythroblastosis and LD in serum are increased. In the early stage, there is a severe thrombocytosis similar to essential thrombocythemia. Anisopoikilocytosis accompanied by red blood cells in the type of a teardrop is shown, and the bone marrow has high cellularity and severe reticulin or collagen fibrosis, leading to bone marrow failure due to bone marrow fibrosis in the terminal stage.

Until now, no clear molecular genetic markers has been reported for polycythaemia vera, essential thrombocythaemia, and primary myelofibrosis classified as Classic MPN. However, in 2005, mutations in the V617F gene of Janus tyrosine kinase 2 (JAK2) have been reported, bringing a new turning point in diagnosis and research thereof. This region corresponds to the pseudokinase autoinhibitory JH2 domain of JAK2 protein, and it was confirmed that the constitutive activation of JAK2 tyrosine kinase by this mutation causes cell proliferation regardless of growth factors. JAK2 V617F mutation caused by c.1849G>T or c.1849_1851delinsTTT base substitution is an important genetic mutation involved in the development of BCR/ABL negative myeloproliferative neoplasm, which is generally detected in 90% to 95% of polycythaemia vera, 35% to 70% of essential thrombocythaemia, and 50% of primary myelofibrosis although there are some differences depending on reports. Therefore, the presence of JAK2 V617F mutation in polycythaemia vera susceptible patients is very useful for diagnosis. However, JAK2 V617F has been detected in 95% or more of polycythaemia vera, but it has not been detected in 30% to 40% or more of essential thrombocythaemia and primary myelofibrosis. Therefore, there has been a continuing need for new molecular genetic markers other than JAK2 V617F.

Second, MPL W515 mutations in which a tryptophan positioned in the thrombopoietin receptor (TPO-R; myeloproliferative leukemia (MPL)) exon 10 was replaced with another amino acid have been reported in a BCR/ABL negative myeloproliferative neoplasm. MPL W515 mutations have been reported primarily in essential thrombocythaemia and primary myelofibrosis in BCR/ABL negative myeloproliferative neoplasm. These mutations were observed in about 7% to 25% of JAK2 V617F negative primary myelofibrosis and 1% to 24% of essential thrombocythaemia. Further, the mutations are very rare in polycythaemia vera in which only two cases have been reported so far. A total of five subtypes of the MPL W515 mutation have been known so far: W515L substituted by leucine; W515K substituted by lysine; W515R substituted by arginine; W515A substituted by alanine; and W515S substituted by serine. Among them, W515L by c.1544G>T base substitution and W515K by c.1543_1544delinsAA base substitution are the most common, which they are observed in 55% and 21%, respectively, in essential thrombocythaemia, and in 93% and 7%, respectively, of primary myelofibrosis, and thus W515L is more commonly observed. Several reports about the association of MPL W515 mutation with clinical features reveal that MPL W515 mutation results in lower hemoglobin and total leukocyte counts and higher platelet counts than JAK2 V617F positive in essential thrombocythaemia. Bone marrow appearance showed relatively lower cellularity and fewer red blood-type hemocyte counts but relatively high megakaryocyte counts.

Recent studies have revealed that the calreticulin gene (CALR) mutation associated with BCR/ABL negative myeloproliferative neoplasm has been observed mainly in patients with JAK2 V617F/MPL W515 mutation negative myeloproliferative neoplasm, which is a novel causative gene causing BCR/ABL negative myeloproliferative neoplasm. In researches by Nangalia J, et al., massively parallel sequencing of 151 patients with BCR/ABL negative myeloproliferative neoplasm was carried out to show frame-shift mutations due to repeated deletion/duplication or insertion in exon 9 of CALR gene encoding calreticulin (Non-patent document 1). Recent studies have shown that the CALR gene mutation was not observed in polycythaemia vera and was found in 67% of patients with JAK2 V617F/MPL W515 mutation negative essential thrombocythaemia and in 88% of patients with primary myelofibrosis (Non-patent document 2). Most of the reported CALR gene mutations (about 80%) were hot spots, which account for about 50% of c.1092_1143del52 base deletions (L367fs*46, type 1) and about 30% of c.1154_1155insTTGTC base insertions (K385fs*47, type 2).

DETAILED DESCRIPTION

Technical Problem

It is very important that a prerequisite for molecular genetic in vitro diagnostic tests as a screening test is to select major gene mutations as detection targets with high sensitivity, which are involved in the molecular genetic pathogenesis of BCR/ABL negative myeloproliferative neoplasm. However, there has been no commercialized in vitro diagnostic test for multiplex detection of BCR/ABL negative myeloproliferative neoplasm-associated gene mutations by the domestic technique, and clinical trial data are shortage and not enough clinical trial data, and thus it is urgent to develop a screening test that incorporates multiplex detection molecular genetic test technology to apply the result to clinical practice.

Technical Solution

In order to address the issues as described above, the present invention provides a peptide nucleic acid probe comprising any one or more selected from the group consisting of nucleic acid sequences represented by SEQ ID NOs: 7 to 10 and nucleic acid sequences complementary to the nucleic acid sequences, which is designed to complementarily bind to a BCR/ABL negative myeloproliferative neoplasm-associated gene to enable multiplex detection of a gene mutation.

According to an embodiment of the present invention, the BCR/ABL negative myeloproliferative neoplasm-associated gene is one or more selected from the group consisting of Janus tyrosine kinase 2 (JAK2), thrombopoietin receptor (MPL), and calreticulin (CALR).

According to an embodiment of the present invention, the gene mutation includes one or more selected from the group consisting of (i) substitution of amino acid valine with phenylalanine at position 617 of the Janus tyrosine kinase 2 gene (JAK2 V617F), (ii) substitution of amino acid tryptophan with leucine at position 515 of the thrombopoietin receptor gene (MPL W515L), (iii) substitution of amino acid tryptophan with lysine at position 515 of the thrombopoietin receptor gene (MPL W515K), (iv) substitution of amino acid tryptophan with arginine at position 515 of the thrombopoietin receptor gene (MPL W515R), (v) substitution of amino acid tryptophan with alanine at position 515 of the thrombopoietin receptor gene (MPL W515A), (vi) substitution of amino acid tryptophan with serine at position 515 of the thrombopoietin receptor gene (MPL W515S), (vii) c.1092_1143del52 base deletion of calreticulin gene (L367fs*46) and (viii) c.1154_1155insTTGTC base insertion of the calreticulin gene (K385fs*47).

According to an embodiment of the present invention, the substitution of amino acid valine with phenylalanine at position 617 of the Janus tyrosine kinase 2 gene (JAK2 V617F) is c.1849G>T or c.1849_1851delinsTTT base substitution.

According to an embodiment of the present invention, the substitution of amino acid tryptophan with leucine at position 515 of the thrombopoietin receptor gene (MPL W515L) is c.1544G>T base substitution.

According to an embodiment of the present invention, the substitution of amino acid tryptophan with lysine at position 515 of the thrombopoietin receptor gene (MPL W515K) is c.1543_1544delinsAA base substitution.

According to an embodiment of the present invention, the peptide nucleic acid probe includes a reporter and a quencher combined with both ends thereof.

According to an embodiment of the present invention, the reporter is selected from the group consisting of FAM (6-carboxyfluorescein), Texas red, HEX (2',4',5',7'-tetrachloro-6-carboxy-4,7-dichlorofluorescein), and Cy5.

According to an embodiment of the present invention, the quencher is selected from the group consisting of TAMRA (6-carboxytetramethyl-rhodamine), BHQ1, BHQ2, and Dabcyl.

The present invention provides a composition for multiplex detection of a BCR/ABL negative myeloproliferative neoplasm-associated gene mutation, which comprises the peptide nucleic acid probe as described above.

The present invention provides a kit for multiplex detection of a BCR/ABL negative myeloproliferative neoplasm-associated gene mutation, which comprises the composition for multiplex detection as described above.

The present invention provides a composition for multiplex detection of a BCR/ABL negative myeloproliferative neoplasm-associated gene mutation, which is designed to complementarily bind to a BCR/ABL negative myeloproliferative neoplasm-associated gene to enable multiplex detection of a gene mutation, in which the composition comprises: (i) a first solution including a peptide nucleic acid probe including at least one selected from the group consisting of nucleic acid sequences represented in SEQ ID NOs: 7 and 9 and nucleic acid sequences complementary to the nucleic acid sequences and a second solution including a peptide nucleic acid probe including at least one selected from the group consisting of nucleic acid sequences represented in SEQ ID NOs: 8 and 10 and nucleic acid sequences complementary to the nucleic acid sequences; or (ii) a first solution including a peptide nucleic acid probe including at least one selected from the group consisting of nucleic acid sequences represented in SEQ ID NOs: 7 and 10 and nucleic acid sequences complementary to the nucleic acid sequences and a second solution including a peptide nucleic acid probe including at least one selected from the group consisting of nucleic acid sequences represented in SEQ ID NOs: 8 and 9 and nucleic acid sequences complementary to the nucleic acid sequences, in which the first solution and the second solution are present in an unmixed state, and the solutions respectively or sequentially contact with a sample of target DNA to result in reaction.

According to an embodiment of the present invention, the peptide nucleic acid probe included in the first solution binds to complementarily one or more of Janus tyrosine kinase 2 (JAK2) gene and calreticulin (CALR) gene, and the peptide nucleic acid probe included in the second solution binds to complementarily one or more of thrombopoietin receptor (MPL) gene and calreticulin (CALR) gene.

According to an embodiment of the present invention, the first solution detects one or more gene mutations selected from the group consisting of (i) substitution of amino acid valine with phenylalanine at position 617 of the janus tyrosine kinase 2 gene (JAK2 V617F) and (ii) c.1092_1143del52 base deletion of calreticulin gene (L367fs*46) or c.1154_1155insTTGTC base insertion of the calreticulin gene (K385fs*47), and the second solution detects one or more gene mutations selected from the group consisting of (i) substitution of amino acid tryptophan with lysine at position 515 of the thrombopoietin receptor gene (MPL W515K), (ii) substitution of amino acid tryptophan with arginine at position 515 of the thrombopoietin receptor gene (MPL W515R), (iii) substitution of amino acid tryptophan with alanine at position 515 of the thrombopoietin receptor gene (MPL W515A), (iv) substitution of amino acid tryptophan with serine at position 515 of the thrombopoietin receptor gene (MPL W515S), and (v) c.1092_1143del52 base deletion of calreticulin gene (L367fs*46) or c.1154_1155insTTGTC base insertion of the calreticulin gene (K385fs*47).

According to an embodiment of the present invention, (i) the substitution of amino acid valine with phenylalanine at position 617 of the janus tyrosine kinase 2 gene (JAK2 V617F) is c.1849G>T or c.1849_1851delinsTTT base substitution, (ii) the substitution of amino acid tryptophan with leucine at position 515 of the thrombopoietin receptor gene (MPL W515L) is c.1544G>T base substitution, and (iii) the substitution of amino acid tryptophan with lysine at position 515 of the thrombopoietin receptor gene (MPL W515K) is c.1543_1544delinsAA base substitution.

The present invention provides a kit for multiplex detection of a BCR/ABL negative myeloproliferative neoplasm-associated gene mutation, which comprises the composition for multiplex detection as described above.

The present invention provides a primer comprising any one or more sequences selected from the group consisting of SEQ ID NOs: 1 to 6, which is designed to complementarily bind to a BCR/ABL negative myeloproliferative neoplasm-associated gene to specifically amplify a region of mutation site.

The present invention provides a method for multiplex detection of a BCR/ABL negative myeloproliferative neoplasm-associated gene mutation, in which the method comprises: hybridizing a product by adding the peptide nucleic acid probe as described above to a target DNA sample; obtaining a melting curve by melting a hybridized product while temperature thereof changes; and comparing the melting curve with standard melting temperatures of mutant genes.

According to an embodiment of the present invention, the hybridizing is performed by mixing the target sample with a primer, amplifying a product by PCR, and then adding the peptide nucleic acid probe to the amplified product.

The present invention provides a method for multiplex detection of a BCR/ABL negative myeloproliferative neoplasm-associated gene mutation, in which the method includes: adding the composition for multiplex detection as described above to a target DNA sample and hybridizing a product by adding a first solution and a second solution respectively or sequentially thereto; obtaining a melting curve by melting a hybridized product while temperature thereof changes; and comparing the melting curve with the standard melting temperature of mutant genes.

According to an embodiment of the present invention, the hybridizing is performed by mixing the target sample with a primer, amplifying a product by PCR, and then adding the composition for multiplex detection to the amplified product.

According to an embodiment of the present invention, the primer includes any one or more sequences selected from the group consisting of SEQ ID NOs: 1 to 6, which is designed to complementarily bind to a BCR/ABL negative myeloproliferative neoplasm-associated gene to specifically amplify a region of mutation site.

According to an embodiment of the present invention, the gene mutation includes one or more selected from the group consisting of (i) substitution of amino acid valine with phenylalanine at position 617 of the Janus tyrosine kinase 2 gene (JAK2 V617F), (ii) substitution of amino acid tryptophan with leucine at position 515 of the thrombopoietin receptor gene (MPL W515L), (iii) substitution of amino acid tryptophan with lysine at position 515 of the thrombopoietin receptor gene (MPL W515K), (iv) substitution of amino acid tryptophan with arginine at position 515 of the thrombopoietin receptor gene (MPL W515R), (v) substitution of amino acid tryptophan with alanine at position 515 of the thrombopoietin receptor gene (MPL W515A), (vi) substitution of amino acid tryptophan with serine at position 515 of the thrombopoietin receptor gene (MPL W515S), (vii) c.1092_1143del52 base deletion of calreticulin gene (L367fs*46) and (viii) c.1154_1155insTTGTC base insertion of the calreticulin gene (K385fs*47).

According to an embodiment of the present invention, the mutation of the substitution of amino acid valine with phenylalanine at position 617 of the Janus tyrosine kinase 2 gene (JAK2 V617F), which is detected by the method is c.1849G>T or c.1849_1851delinsTTT base substitution.

According to an embodiment of the present invention, the mutation of the substitution of amino acid tryptophan with leucine at position 515 of the thrombopoietin receptor gene (MPL W515L), which is detected by the method is c.1544G>T base substitution.

According to an embodiment of the present invention, the mutation of the substitution of amino acid tryptophan with lysine at position 515 of the thrombopoietin receptor gene (MPL W515K), which is detected by the method is c.1543_1544delinsAA base substitution.

Advantageous Effects

The present invention provides a peptide nucleic acid probe capable of rapidly and accurately multiple-detecting BCR/ABL negative myeloproliferative neoplasm-associated gene mutations, which is used to detect the gene mutations effectively. Further, one detection process is carried out to rapidly and effectively multiple-detect BCR/ABL negative myeloproliferative neoplasm-associated gene mutations, which is useful for disease diagnosis, follow-up, prognosis estimation, and treatment.

BRIEF DESCRIPTION OF THE DRAWINGS

FIG. 1 is the diagram illustrating positions of base mutations of JAK2 gene, a PNA probe, and a primer.

FIG. 2 is the diagram illustrating positions of base mutations of MPL gene, a PNA probe, and a primer.

FIG. 3 is the diagram illustrating positions of base mutations of CALR gene, a PNA probe, and a primer.

FIG. 4 illustrates melting curve graphs obtained by using a synthetic DNA and a peptide nucleic acid probe detecting JAK2-2 mutation according to an embodiment of the present invention.

FIG. 5 illustrates melting curve graphs obtained by using a synthetic DNA and a peptide nucleic acid probe detecting MPL-3 mutation according to an embodiment of the present invention.

FIG. 6 illustrates melting curve graphs obtained by using a synthetic DNA and a peptide nucleic acid probe detecting CALR-del4 mutation according to an embodiment of the present invention.

FIG. 7 illustrates melting curve graphs obtained by using a synthetic DNA and a peptide nucleic acid probe detecting CALR-ins5p mutation according to an embodiment of the present invention.

FIG. 8 illustrates melting curve graphs of related gene mutations obtained by using DNA of BCR/ABL negative myeloproliferative neoplasm patients according to an embodiment of the invention.

FIG. 9 illustrates melting curve graphs of related gene mutations obtained by using DNA of patients with BCR/ABL negative myeloproliferative neoplasm.

FIG. 10 illustrates melting curve graphs obtained by using a synthetic DNA and a peptide nucleic acid probe detecting various mutations of JAK2 gene.

FIG. 11 illustrates melting curve graphs obtained by using a synthetic DNA and a peptide nucleic acid probe detecting various mutations of MPL gene.

FIG. 12 illustrates melting curve graphs obtained by using a synthetic DNA and a peptide nucleic acid probe detecting various deletion mutations of CALR gene.

FIG. 13 illustrates melting curve graphs obtained by using a sample and a peptide nucleic acid probe detecting deletion mutations of CALR gene.

FIG. 14 illustrates melting curve graphs obtained by using a synthetic DNA and a peptide nucleic acid probe detecting various insertion mutations of CALR gene.

FIGS. 15a-15b illustrate the result of confirming the sensitivity of composition which is divided into the first solution (A set) and the second solution (B set) to minimize the interference effect of the composition of the present composition.

FIGS. 16a-16c illustrate the result of confirming the detection limit of the composition of the present invention, which is divided into the first solution (A set) and the second solution (B set).

FIG. 17 illustrates the results of confirming the sensitivity of the composition of the present invention, which is divided into the first solution (A set) and the second solution (B set).

FIG. 18 illustrates the results of verifying the specificity of the composition of the present invention, which is divided into the first solution (A set) and the second solution (B set).

FIG. 19 illustrates the result of verifying multiplex detection of the same causative gene of the composition of the present invention, which is divided into the first solution (A set) and the second solution (B set).

FIGS. 20a-20b illustrate the result of verifying multiplex detection of different causative genes of the composition of the present invention, which is divided into the first solution (A set) and the second solution (B set).

FIGS. 21a-21b illustrate the result of verifying multiplex detection of six causative genes of the composition of the present invention, which is divided into the first solution (A set) and the second solution (B set).

BEST MODE

In order to accomplish the objects as described above, the present invention provides a peptide nucleic acid probe designed to complementarily bind to a BCR/ABL negative myeloproliferative neoplasm-associated gene to enable multiplex detection of a gene mutation, which includes any one or more selected from the group consisting of nucleic acid sequences represented by SEQ ID NOs: 7 to 10 and nucleic acid sequences complementary to the nucleic acid sequences, a composition for multiplex detection of gene mutations including the same, a kit, and a method for multiplex detection of BCR/ABL negative myeloproliferative neoplasm-associated gene mutations using the same. Hereinafter, the present invention is described in detail with reference to the drawings.

It is to be understood that terms employed herein are for the purpose of description of particular embodiments and not of limitation. The singular forms include plural referents unless otherwise stated. Further, it should be understood that terms "include" or "have" are inclusive of characteristics, numerals, steps, operations, elements, parts or combination thereof, which are described herein, but are not exclusive of presence or addition of one or more different characteristics, numerals, steps, operations, elements, parts or combination thereof. Although the terms "first," "second," and the like are used herein to describe various elements, these elements should not be limited by these terms. These terms are only used to distinguish one element from another element.

As used herein, the term "target nucleic acid" refers to the nucleic acid sequence to be detected, and the target nucleic acid and a primer or a probe are annealed or hybridized under hybridization, annealing or amplification conditions. The term "target nucleic acid" is not different from and used interchangeably with the term "target nucleic acid sequence" or "target sequence" as used herein.

As used herein, the term "hybridization" means that complementary single-stranded nucleic acids form a double-stranded nucleic acid. Hybridization can occur when the complementarity between two nucleic acid strands is perfect (perfect match) or when some mismatched residues exist. The complementarity level for hybridization may vary depending on hybridization conditions and may be particularly controlled by the temperature.

As used herein, the term "gene mutation" refers to a mutation in the nucleic acid sequence of the target nucleic acid, which is characterized by including not only a single nucleotide polymorphism (SNP) but also mutations of base substitution, deletion or insertion. Further, peptide nucleic acid (PNA) probe of the present invention can analyze the SNP of the target nucleic acid or the mutation caused by the base substitution, deletion or insertion of the target nucleic acid by melting curve analysis.

The present invention provides a peptide nucleic acid probe designed to complementarily bind to a BCR/ABL negative myeloproliferative neoplasm-associated gene to enable multiplex detection of a gene mutation, which includes any one or more selected from the group consisting of nucleic acid sequences represented by SEQ ID NOs: 7 to 10 and nucleic acid sequences complementary to the nucleic acid sequences. More particularly, the gene mutation of the target nucleic acid is multiplex detected. For example, the BCR/ABL negative myeloproliferative neoplasm-associated gene includes any one or more selected from the group consisting of Janus tyrosine kinase 2 (JAK2), thrombopoietin receptor (MPL), and calreticulin (CALR).

More specifically, the gene mutation preferably includes (i) substitution of amino acid valine with phenylalanine at position 617 of the janus tyrosine kinase 2 gene (JAK2 V617F), (ii) substitution of amino acid tryptophan with leucine at position 515 of the thrombopoietin receptor gene (MPL W515L), (iii) substitution of amino acid tryptophan with lysine at position 515 of the thrombopoietin receptor gene (MPL W515K), (iv) substitution of amino acid tryptophan with arginine at position 515 of the thrombopoietin receptor gene (MPL W515R), (v) substitution of amino acid tryptophan with alanine at position 515 of the thrombopoietin receptor gene (MPL W515A), (vi) substitution of amino acid tryptophan with serine at position 515 of the thrombopoietin receptor gene (MPL W515S), (vii)

c.1092_1143del52 base deletion of calreticulin gene (L367fs*46), and (viii) c.1154_1155insTTGTC base insertion of the calreticulin gene (K385fs*47). For example, the substitution of amino acid valine with phenylalanine at position 617 of the Janus tyrosine kinase 2 gene (JAK2 V617F) may be c.1849G>T or c.1849_1851delinsTTT base substitution. Further, the substitution of amino acid tryptophan with leucine at position 515 of the thrombopoietin receptor gene (MPL W515L) may be c.1544G>T base substitution. Further, the substitution of amino acid tryptophan with lysine at position 515 of the thrombopoietin receptor gene (MPL W515K) may be c.1543_1544delinsAA base substitution.

Further, in the present invention, the Janus tyrosine kinase 2 gene includes the nucleic acid sequence described in JAK2_NM_004972.3, which is NCBI number, and the amino acid sequence thereof may include the amino acid sequence described in NP_004963.1.

Further, the thrombopoietin receptor gene includes the nucleic acid sequence described in MPL_NM_005373.2, which is NCBI number, and the amino acid sequence thereof may include the amino acid sequence described in NP_005364.1.

Further, the calreticulin gene includes the nucleic acid sequence described in CALR_NM_004343.3, which is NCBI number, and the amino acid sequence thereof may include the amino acid sequence described in NP_004334.1.

It is very important that a prerequisite for molecular genetic in vitro diagnostic tests as a screening test is to select mutations that are frequently observed in the JAK2, MPL, and CALR genes as detection targets with high sensitivity, which are involved in the molecular genetic pathogenesis of BCR/ABL negative myeloproliferative neoplasm. Therefore, JAK2 V617F, MPL W515L/K, and CALR L367fs*46/K385fs*47 mutations are selected as detection targets. In development and commercialization of a test kit for multiplex detection for screening and diagnosis of related mutations (JAK2 V617F, MPL W515L/K, CALR L367fs*46/K385fs*47 mutations) for the sub-classification on the diagnosis of BCR/ABL negative myeloproliferative neoplasm, the treatment strategies of BCR/ABL negative myeloproliferative neoplasm are different. Therefore, accurate diagnosis is very important in the suspected new cases, and detection of the related gene mutation is useful for improving the accuracy of the diagnosis. Accordingly, the present invention enables rapid and accurate multiplex detection of the presence of JAK2 V617F, MPL W515L/K, and CALR L367fs*46/K385fs*47 mutations as representative mutations.

The length of the PNA according to the present invention is not particularly limited but may be 9 mer to 16 mer which includes SNP and Indel of JAK2, MPL, and CALR that are related to BCR/ABL negative myeloproliferative neoplasm. The probe may be designed to have the desired Tm value by adjusting the length of PNA probe. Tm value may be adjusted by changing the nucleic acid sequence thereof even if PNA probe has the same length. Further, since PNA has better binding ability than DNA to have a higher basic Tm value, it can be designed shorter than DNA to enable detection of SNP that is close thereto. According to the conventional HRM method, the difference of the Tm values is very low at about 0.5° C., and thus, additional analysis programs or fine temperature changes or calibration are required. Therefore, when two or more SNPs appear, the analysis is difficult. However, PNA probe according to the present invention is not affected by probe sequences and SNP, thereby enabling easy analysis.

A reporter and a quencher may be attached to both ends of the peptide nucleic acid probe. The reporter may be selected from the group consisting of FAM (6-carboxyfluorescein), Texas red, HEX (2',4',5',7',-tetrachloro-6-carboxy-4,7-dichlorofluorescein), and Cy5, and the quencher may be selected from the group consisting of TAMRA (6-carboxytetramethyl-rhodamine), BHQ1, BHQ2, and Dabcyl.

The present invention provides a composition for multiplex detection of a BCR/ABL negative myeloproliferative neoplasm-associated gene mutation including the peptide nucleic acid probe as described above.

The present invention provides a kit for multiplex detection of a BCR/ABL negative myeloproliferative neoplasm-associated gene mutation, which includes the composition for multiplex detection as described above. The kit may optionally include reagents necessary to carry out a target amplification reaction (for example, PCR reaction) such as a buffer, a DNA polymerase co-factor, and deoxyribonucleotide-5-triphosphate. Further, the kit of the present invention may include various polynucleotide molecules, reverse transcriptase, various buffers and reagents, and antibodies that inhibit DNA polymerase activity. The kit as described above is used to multiplex detect a single base mutation and mutations due to a deletion or insertion of a base of a target nucleic acid through analysis of a melting curve by a PNA probe, thereby enabling multiplex detection of the presence or absence of BCR/ABL negative myeloproliferative neoplasm-associated gene mutations.

The present invention provides a composition for multiplex detection of a BCR/ABL negative myeloproliferative neoplasm-associated gene mutation, which is designed to complementarily bind to the BCR/ABL negative myeloproliferative neoplasm-associated gene to enable multiplex detection of gene mutations. The composition includes (i) a first solution including a peptide nucleic acid probe including at least one selected from the group consisting of nucleic acid sequences represented in SEQ ID NOs: 7 and 9 and nucleic acid sequences complementary to the nucleic acid sequences and a second solution including a peptide nucleic acid probe including at least one selected from the group consisting of nucleic acid sequences represented in SEQ ID NOs: 8 and 10 and nucleic acid sequences complementary to the nucleic acid sequences; or (ii) a first solution including a peptide nucleic acid probe including at least one selected from the group consisting of nucleic acid sequences represented in SEQ ID NOs: 7 and 10 and nucleic acid sequences complementary to the nucleic acid sequences and a second solution including a peptide nucleic acid probe including at least one selected from the group consisting of nucleic acid sequences represented in SEQ ID NOs: 8 and 9 and nucleic acid sequences complementary to the nucleic acid sequences. The first solution and the second solution are present in an unmixed state. The solutions respectively or sequentially contact with a sample of target DNA to result in reaction thereof.

This configuration as described above results in minimizing the interference phenomenon or the binding interruption phenomenon between peptide nucleic acid probes binding to the same or similar gene position, thereby enabling more precise and accurate detection. In other words, when the peptide nucleic acid probe for Janus tyrosine kinase 2 (JAK2) and the peptide nucleic acid probe for thrombopoietin receptor (MPL) are mixed and processed at the same time, self-extinction due to the interference between the two probes may occur to decrease the accuracy and sensitivity of detection of the mutation of substitution of amino acid valine with phenylalanine at position 617 of the Janus tyrosine kinase 2 gene (JAK2 V617F). Further, in order to detect the deletion and addition of nucleic acid sequence of calreticulin (CALR) gene, when the respective peptide nucleic acid probes are mixed and processed at the same time, the binding sites of the two probes may be too close to each other, thereby reducing the accuracy and sensitivity for detection of base deletion mutations of calreticulin gene during binding process thereof. Therefore, the issue can be solved by appropriately dividing them into a first solution and a second solution. The term "first solution" or "second solution" refers that when two or more peptide nucleic acid probes are mixed, they are divided and mixed in two or more solutions to prepare a composition for detection instead of mixing them in one solution. Further, it does not mean the order of detection or contact with a target DNA sample.

According to an embodiment of the present invention, the peptide nucleic acid probe included in the first solution of the composition for multiplex detection of gene mutations may bind to complementarily one or more of Janus tyrosine kinase 2 (JAK2) gene and calreticulin (CALR) gene, and the peptide nucleic acid probe included in the second solution may bind to complementarily one or more of thrombopoietin receptor (MPL) gene and calreticulin (CALR) gene.

According to an embodiment of the present invention, the first solution of the composition for multiplex detection of gene mutations may detect one or more gene mutations selected from the group consisting of (i) substitution of amino acid valine with phenylalanine at position 617 of the janus tyrosine kinase 2 gene (JAK2 V617F) and (ii) c.1092_1143del52 base deletion of calreticulin gene (L367fs*46) or c.1154_1155insTTGTC base insertion of the calreticulin gene (K385fs*47), and the second solution may detect one or more gene mutations selected from the group consisting of (i) substitution of amino acid tryptophan with lysine at position 515 of the thrombopoietin receptor gene (MPL W515K), (ii) substitution of amino acid tryptophan with arginine at position 515 of the thrombopoietin receptor gene (MPL W515R), (iii) substitution of amino acid tryptophan with alanine at position 515 of the thrombopoietin receptor gene (MPL W515A), (iv) substitution of amino acid tryptophan with serine at position 515 of the thrombopoietin receptor gene (MPL W515S), and (v) c.1092_1143del52 base deletion of calreticulin gene (L367fs*46) or c.1154_1155insTTGTC base insertion of the calreticulin gene (K385fs*47).

The present invention provides a kit for multiplex detection of a BCR/ABL negative myeloproliferative neoplasm-associated multiplex gene mutations, which includes the composition for multiplex detection as described above.

The present invention provides a primer comprising any one or more sequences selected from the group consisting of SEQ ID NOs: 1 to 6, which is designed to complementarily bind to a BCR/ABL negative myeloproliferative neoplasm-associated gene to specifically amplify a region of mutation site.

According to an embodiment of the present invention, the present invention provides a method for multiplex detection of a BCR/ABL negative myeloproliferative neoplasm-associated gene mutation, in which the method comprises: hybridizing a product by adding the peptide nucleic acid probe as described above to a target DNA sample; obtaining a melting curve by melting a hybridized product while temperature thereof changes; and comparing the melting curve with standard melting temperatures of mutant genes.

The present inventors compared and analyzed JAK2, MPL, and CALR genes related to BCR/ABL negative myeloproliferative neoplasm and produced PNAs including each of one or more nucleic acid sequences selected from the group consisting of the nucleic acid sequences exhibited in Table 2. These PNAs were used to obtain a melting curve from the sample of BCR/ABL negative myeloproliferative neoplasm patients. The melting temperature (Tm) was confirmed from the melting curve, and as a result, different results according to gene mutations were obtained as confirmed in examples as described below.

The process of hybridization is to react the PNA according to the present invention with a DNA sample of a patient who is suspected to have BCR/ABL negative myeloproliferative neoplasm. The hybridization process may be a process in which the target sample is mixed with a primer, a product is amplified by PCR, and then the peptide nucleic acid probe is added to the amplified product to perform hybridization thereof. In other words, the hybridization process may include a PCR process and may use a forward/reverse primer set for PCR. Such hybridization process and PCR condition may include all of the various methods well known to those of ordinary skill in the art (hereinafter, referring as to "those skilled in the art"). Further, it may include a melting process after completing PCR.

Next, the process of obtaining the melting curve by temperature is to obtain the melting temperature (Tm) of a DNA sample of a patient who is suspected to have BCR/ABL negative myeloproliferative neoplasm. For this purpose, fluorescence intensities are measured while increasing the temperature of the hybridized product. Therefore, a melting curve according to temperature can be obtained from the change in fluorescence intensity with temperature. In other words, a fluorescence melting curve analysis (FMCA) can be used as a hybridization method analysis. In FMCA, Tm is used to sort the difference in binding force between the product obtained after completion of the PCR reaction and the probe added, thereby enabling the analysis thereof. For example, the Tm value can be obtained by measuring the intensity of fluorescence every 1° C. increase by using a general real-time PCR device.

Next, the process of multiplex detection of the BCR/ABL negative myeloproliferative neoplasm-associated gene mutations is performed by multiplex detection of presence or absence and types of gene mutations from the melting temperature of the obtained melting curve. For example, the melting temperature of the obtained melting curve can be compared with the melting temperature according to the differences in gene mutations, which have already been known, thereby enabling multiplex detection of the presence or absence and types of the base mutation. Melting curves by gene mutations using PNA according to the present invention have different melting temperatures (Tm) (See FIGS. 4 to 7). Such differences may be used to allow the multiplex detection of the presence or absence and types of gene mutations.

The present invention provides a method for multiplex detection of a BCR/ABL negative myeloproliferative neoplasm-associated gene mutation, in which the method includes: respectively or sequentially adding the composition for multiplex detection of gene mutations, which is divided into the first solution and the second solution to a target DNA sample, thereby enabling hybridization while minimizing the interfere phenomenon as described above; obtaining a melting curve by melting a hybridized product while temperature thereof changes; and comparing the melting curve with the standard melting temperature of mutant genes. This may minimize the interference phenomenon which can occur when multiplex genes are detected at the same time.

A composition for multiplex detection of gene mutations configured to be divided into the first solution and the second solution for minimizing the interference phenomenon is a composition for multiplex detection of a BCR/ABL negative myeloproliferative neoplasm-associated gene mutation, which is designed to complementarily bind to the BCR/ABL negative myeloproliferative neoplasm-associated gene to enable multiplex detection of gene mutations, in which the composition includes: (i) a first solution including a peptide nucleic acid probe including at least one selected from the group consisting of nucleic acid sequences represented in SEQ ID NOs: 7 and 9 and nucleic acid sequences complementary to the nucleic acid sequences and a second solution including a peptide nucleic acid probe including at least one selected from the group consisting of nucleic acid sequences represented in SEQ ID NOs: 8 and 10 and nucleic acid sequences complementary to the nucleic acid sequences; or (ii) a first solution including a peptide nucleic acid probe including at least one selected from the group consisting of nucleic acid sequences represented in SEQ ID NOs: 7 and 10 and nucleic acid sequences complementary to the nucleic acid sequences and a second solution including a peptide nucleic acid probe including at least one selected from the group consisting of nucleic acid sequences represented in SEQ ID NOs: 8 and 9 and nucleic acid sequences complementary to the nucleic acid sequences, in which the first solution and the second solution are present in an unmixed state, and the solutions respectively or sequentially contact with a sample of target DNA to result in reaction.

According to an embodiment of the present invention, the hybridization process is performed by mixing the target sample with a primer, amplifying a product by PCR, and then adding the composition for multiplex detection to the amplified product.

The primer may include any one or more sequences selected from the group consisting of SEQ ID NOs: 1 to 6, which is designed to complementarily bind to a BCR/ABL negative myeloproliferative neoplasm-associated gene to specifically amplify a region of mutation site.

The gene mutation detected by the method as described above may include one or more selected from the group consisting of (i) substitution of amino acid valine with phenylalanine at position 617 of the janus tyrosine kinase 2 gene (JAK2 V617F), (ii) substitution of amino acid tryptophan with leucine at position 515 of the thrombopoietin receptor gene (MPL W515L), (iii) substitution of amino acid tryptophan with lysine at position 515 of the thrombopoietin receptor gene (MPL W515K), (iv) substitution of amino acid tryptophan with arginine at position 515 of the thrombopoietin receptor gene (MPL W515R), (v) substitution of amino acid tryptophan with alanine at position 515 of the thrombopoietin receptor gene (MPL W515A), (vi) substitution of amino acid tryptophan with serine at position 515 of the thrombopoietin receptor gene (MPL W515S), (vii) c.1092_1143del52 base deletion of calreticulin gene (L367fs*46), and (viii) c.1154_1155insTTGTC base insertion of the calreticulin gene (K385fs*47).

The mutation of the substitution of amino acid valine with phenylalanine at position 617 of the Janus tyrosine kinase 2 gene (JAK2 V617F) which is detected by the method may be c.1849G>T or c.1849_1851delinsTTT base substitution. The mutation of the substitution of amino acid tryptophan with leucine at position 515 of the thrombopoietin receptor gene (MPL W515L), which is detected by the method may be c.1544G>T base substitution. The mutation of the substitution of amino acid tryptophan with lysine at position 515 of the thrombopoietin receptor gene (MPL W515K), which is detected by the method may be c.1543_1544delinsAA base substitution.

EXAMPLES

Hereinafter, the present invention will be described in more detail with reference to Examples. It will be to be understood, however, that these Examples are only for illustrative purposes and are not to be construed as limiting the scope of the present invention.

Example 1

Preparation of Peptide Nucleic Acid for Multiplex Detection of Bcr/Abl Negative Myeloproliferative Neoplasm-Associated Gene Mutations.

In this Example, JAK2, MPL, and CALR genes were selected from various BCR/ABL negative myeloproliferative neoplasm associated genes. Primers of JAK2, MPL, and CALR were prepared to perform PCR using DNA of a patient who was suspected to have BCR/ABL negative myeloproliferative neoplasm as a template.

Figure 2:
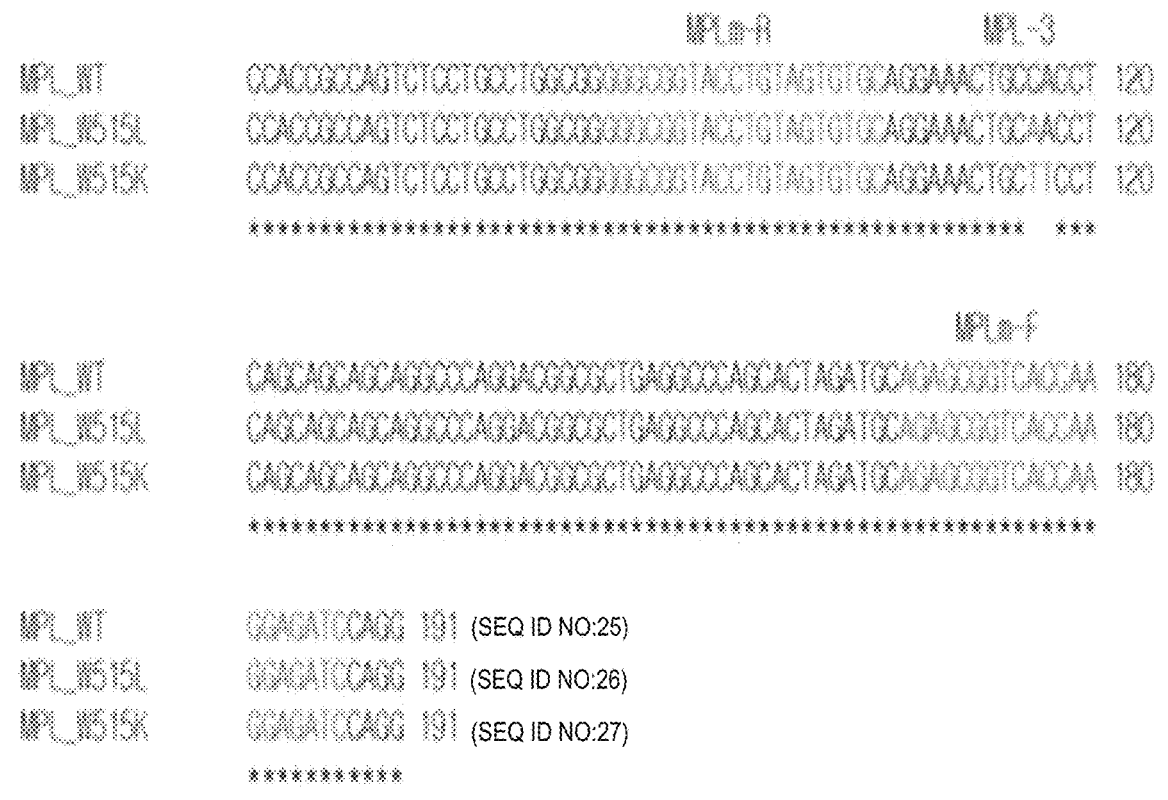
Figure 3:
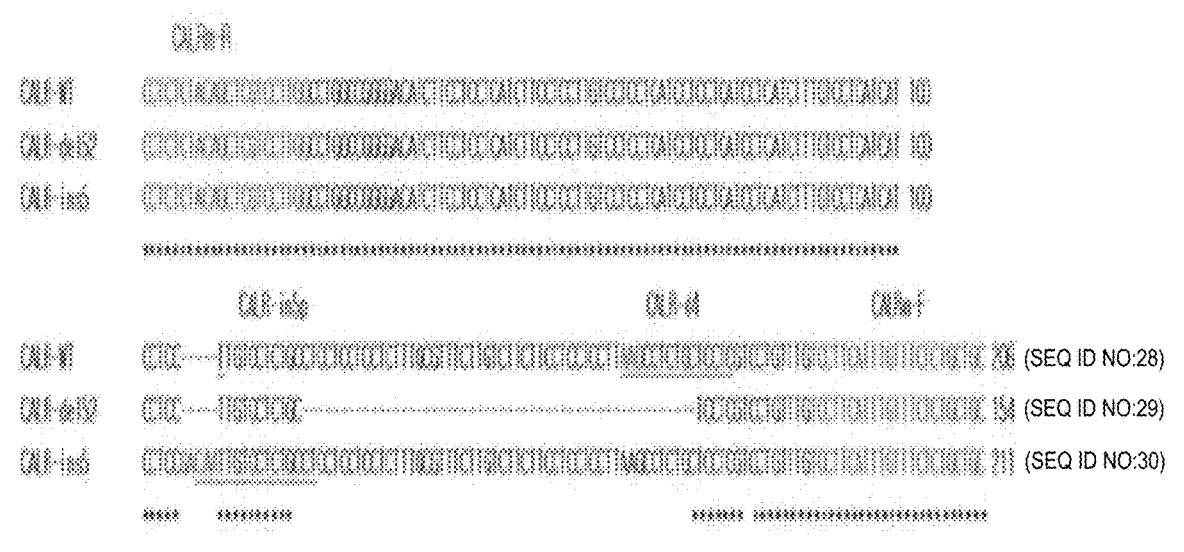

FIGS. 1 to 3 are nucleic acid sequence diagrams illustrating nucleic acid sequence examples of a region of JAK2, MPL and CALR gene, SNP and Indel, and PNA derived therefrom according to the present invention. In FIGS. 1 to 3, the base mutation by each gene is indicated by red. Based on this, the nucleic acid sequence of PNA according to the present invention is indicated in the yellow box, and the primer is indicated by red at the beginning and end of the base.

Thus, primer nucleic acid sequences for gene amplification according to the present invention were determined and exhibited in Table 1 below.

TABLE 1

| Name | Orientation | Nucleic acid sequence (5'-3') | Length (bp) | Melting temperature (° C.) | Size (bp) | |
|---|---|---|---|---|---|---|
| JAK2m | F (Forward) | AGCAGCAAGTATGATGA GCAAGC (SEQ ID NO 1) | 23 | 63.10 | 122 | |
| | R (Reverse) | CAGATGCTCTGAGAAAG GCATTA (SEQ ID NO 2) | 23 | 60.87 | | |
| MPLm | F | GATCTCCTTGGTGACCGC TCT (SEQ ID NO 3) | 21 | 63.00 | 102 | |
| | R | GGGCGGTACCTGTAGTG TGC (SEQ ID NO 4) | 20 | 62.82 | | |
| CALRm | F | GCAGCAGAGAAACAAAT GAAGGA (SEQ ID NO 5) | 23 | 62.94 | 206 | Deletion (del) = 154 |
| | R | CCTCTCTACAGCTCGTCC TTGG (SEQ ID NO 6) | 22 | 62.68 | | Insertion (ins) = 211 |

TABLE 2

| Name | Gene mutation | Nucleic acid sequence (5'-3' Fluorescence) | Perfect match target |
|---|---|---|---|
| JAK2-2 | V317F(TTC, TTT) | Dabcyl-GTATGTGTCTGTGG-O-K(Cy5) (SEQ ID NO 7) | Wild type |
| MPL-3 | W515L, W515K | Dabcyl-CTGAGGTGGCAGT-O-K(FAM) (SEQ ID NO 8) | Wild type |
| CALR-d4 | 1092_1143del52 | Dabcyl-AAGCCTCTGCTCCTC-O-K(HEX) (SEQ ID NO 9) | Wild type |
| CALR-in5p | 1154_1155insTTGTC | Dabcyl-CAATTGTCCTCTGCC-O-K(Texas Red) (SEQ ID NO 10) | c.1154_1155insTTGTC |

*In Table 2, O refers to a linker, and K refers to lysine.

The PNA probe was a combination of three primer sets and four PNA probes in the form of a multiplex in which all four probes were carried out in one tube. The combination was designed so that the same fluorescence did not overlap. Then, a PNA probe according to the present invention was prepared with the nucleic acid sequences exhibited in Table 2, the reporter, and the quencher. All the PNA probes (FAM, HEX, Texas Red, Cy5-labeled, Dabcyl) used in the present invention were synthesized by HPLC purification method from Panagene (Korea), and mass spectrometry was used to confirm the purity of all synthesized probes. Further, the unnecessary secondary structure of the probe was avoided for more effective binding with the target nucleic acid.

Example 2

Melting Curve Analysis of Peptide Nucleic Acid for Multiplex Detection of BCR/ABL Negative Myeloproliferative Neoplasm-Associated Gene Mutation.

The PNA of the present invention prepared according to Example 1 was used to derive a melting curve for a DNA sample of BCR/ABL negative myeloproliferative neoplasm-associated gene mutations. CFX96™ Real-Time system (BIO-RAD, USA) was used to perform the melting curve analysis. The conditions of the asymmetric PCR are as follows: 0.5 μl of the probe (PNA probe prepared in Example 1) and 1 μl of the synthetic gene base mutation DNA (Neo Probe, Korea, Table 3) were added to 10 μl of 2×qPCR PreMix (Seasunbio, Korea) such that that the total volume was 20 and then the melting curve analysis was carried out.

TABLE 3

| | Name | Nucleic acid sequence (5'-3') | Type |
|---|---|---|---|
| 1 | JAK2_PM | GTCTCCACAGACACATACTCC (SEQ ID NO 11) | JAK2 Wild type |
| 2 | JAK2_1MM | GTCTCCACAGAAACATACTCC (SEQ ID NO 12) | JAK2 V617F (TTC) |
| 3 | JAK2_2MM | GTCTCCACAAAAACATACTCC (SEQ ID NO 13) | JAK2 V617F (TTT) |
| 4 | MPL-3_PM | TGCTGAGGTGGCAGTTTC (SEQ ID NO 14) | MPL Wild type |
| 5 | MPL-3_MM1 | TGCTGAGGTTGCAGTTTC (SEQ ID NO 15) | MPL W515L (TTG) |
| 6 | MPL-3_MM2 | TGCTGAGGAAGCAGTTTC (SEQ ID NO 16) | MPL W515K (AAG) |
| 7 | CALR-d4_PM | ACGAGGAGCAGAGGCTTAA (SEQ ID NO 17) | CALR Wild type |
| 8 | CALR-d4_MM | ACGAGGAGCAGAGGACAA (SEQ ID NO 18) | CALR del52 (c.1092_1143del52) |
| 9 | CALR-ins5p_PM | GGAGGCAGAGGACAATTGTC (SEQ ID NO 19) | CALR ins5 (c.1154_1155insTTGTC) |
| 10 | CALR-ins5p_MM1 | GGAGGCAGAGGACAAGGAGG (SEQ ID NO 20) | CALR Wild type |
| 11 | CALR-ins5p_MM2 | CGAGGAGCAGAGGACAAGGAGG (SEQ ID NO 21) | NOCALR Wild type |

FIGS. 4 to 6 illustrate melting peaks for obtaining Tm values in the process of hybridizing a synthetic DNA sample having PNA probes and gene mutations according to Example of the present invention and increasing the temperature of the hybridized product. Here, in the melting process of the real-time PCR device, the denaturalization was carried out at 95° C. for 3 minutes, then the reaction was performed at 75° C. for 30 seconds, at 65° C. for 30 seconds, at 55° C. for 30 seconds, at 45° C. for 30 seconds, at 35° C. for 30 seconds, at 25° C. for 30 seconds, and at 20° C. for 50 seconds. Then, it was heated up to 80° C. by 1° C. and waited for 10 seconds, and then fluorescence thereof was measured. This was why the PNA probes were able to be accurately hybridized with the synthesized DNA oligomer.

TABLE 4

| Probe | Gene mutation | Wild type | Gene mutation | Heterozygote (Mutation type & Wild type) | Heterozygote (Mutation type & Mutation type) |
|---|---|---|---|---|---|
| JAK2-2 | V617F (TTC) | 60 ± 3° C. | 46 ± 3° C. | 46° C. & 60° C. | 30° C. & 46° C. |
|  | V617F (TTT) |  | 30 ± 3° C. | 30° C. & 60° C. |  |
| MPL-3 | W515L | 70 ± 3° C. | 57 ± 3° C. | 57° C. & 70° C. | 44° C. & 57° C. |
|  | W515K | 70 ± 3° C. | 44 ± 3° C. | 44° C. & 70° C. |  |
| CALR-d4 | del52 | 62 ± 3° C. | 50 ± 3° C. | 50° C. & 62° C. | — |
| CALR-in5p | ins5 | 55 ± 3° C. | 63 ± 3° C. | 63° C. & 55° C. | — |

Table 4 exhibits the Tm values derived from the hybridization reaction as described above. Gene mutations can be confirmed by the analysis of Tm values. Further, the prepared PNA probes collected different Tm values for each gene mutation to detect base mutations to unknown target nucleic acids.

Example 3

Analysis of Melting Curves of Peptide Nucleic Acids Using Sample DNA of BCR/ABL Negative Myeloproliferative Neoplasm-Associated Patient.

The PNA of the present invention prepared according to Example 1 was used to derive a melting curve for a DNA sample of BCR/ABL negative myeloproliferative neoplasm-associated gene mutations.

CFX96™ Real-Time system (BIO-RAD, USA) was used to perform the PCR. The asymmetric PCR was used for all experimental conditions to generate a single-stranded target nucleic acid. The conditions of the asymmetric PCR are as follows: 0.5 μl of four types of the probes (PNA probes prepared in Example 1) and 1 μl of DNA of the suspected patient with BCR/ABL negative myeloproliferative neoplasm were added to 2×qPCR PreMix (Seasunbio, Korea), 0.05 μM forward primer and 0.5 μM reverse primer (asymmetric PCR) such that the total volume was 20 μl, the rest was supplemented with DW, and then the real-time PCR was carried out.

FIG. 8 is a graph for explaining an example of a process of hybridizing BCR/ABL negative myeloproliferative neoplasm patient DNA and increasing the temperature of the hybridized product according to an embodiment of the present invention. As illustrated herein, in the real-time PCR process, the denaturalization was carried out at 95° C. for 10 minutes, and then the reaction was performed at 95° C. for 30 seconds, at 58° C. for 30 seconds, and at 74° C. for 45 seconds. This was repeated for 40 cycles, and fluorescence thereof was measured in real time. For the analysis of the melting curve, the denaturalization was carried out at 95° C. for 3 minutes, and then the reaction was performed at 75° C. for 30 seconds, at 65° C. for 30 seconds, at 55° C. for 30 seconds, at 45° C. for 30 seconds, at 35° C. for 30 seconds, at 25° C. for 30 seconds, and at 20° C. for 50 seconds. Then, while it was heated up to 80° C. by 1° C., the fluorescence thereof was measured to perform the analysis of the melting curve. The stationary state was maintained for 10 seconds between steps thereof (See FIG. 8).

FIG. 9 illustrates examples of melting curve graphs by temperature, which were obtained by applying each peptide nucleic acid according to the present invention to DNA of BCR/ABL negative myeloproliferative neoplasm patients. In FIG. 9, six melting curves were performed in a single tube including four probes and three PCR primer sets at the same time, which indicates fluorescence with the corresponding mutation types. Tm values and melting peaks of wild type were observed in all other genes except for the mutation types. The front three are JAK2-2 (Cy5), JAK2-2 (Cy5) and MPL-3 (FAM) from the left and the rear three are MPL-3 (FAM), CALR-ins5p (Texas Red), CALR-d4 (HEX) from the left. As illustrated in FIG. 9, it was confirmed that the melting curves in which PNA according to the present invention was applied to DNA of BCR/ABL negative myeloproliferative neoplasm patients had different melting temperatures (Tm) from each other. Further, it can be seen that different melting temperature (Tm) difference occurs compared with wild type DNA.

TABLE 5

| Sample | JAK2-2 | MPL-3 | CALR-d4 | CALR-in5p | Gene Mutation |
|---|---|---|---|---|---|
| No. 1 | 30° C. & 60° C. | 70° C. | 62° C. | 55° C. | JAK2 V617F |
| No. 2 | 46° C. | 70° C. | 62° C. | 55° C. | JAK2 V617F |
| No. 3 | 60° C. | 44° C. & 70° C. | 62° C. | 55° C. | MPL W515K |
| No. 4 | 60° C. | 57° C. & 70° C. | 62° C. | 55° C. | MPL W515L |
| No. 5 | 60° C. | 70° C. | 62° C. | 55° C. & 63° C. | CALR ins5 |
| No. 6 | 60° C. | 70° C. | 50° C. & 62° C. | 55° C. | CALR del52 |

* Bold indicates the results including BCR/ABL negative myeloproliferative neoplasm-associated gene mutations.

Table 5 is a table summarizing the melting temperature (Tm) obtained from the melting curve graph for each temperature in FIG. 9. In Table 5, the bold and underlined items (indicated by the temperature) indicate that the corresponding gene mutations are present. Base mutations of JAK2, MPL and CALR genes can be multiplex detected based on the Tm values exhibited in Table 5.

Example 4

Selection Process of Effective Peptide Nucleic Acid Probe for Detection of Gene Mutation.

In order to select an effective peptide nucleic acid probe for detection of gene mutations, peptide nucleic acid probes for various gene mutations of JAK2, MPL and CALR genes was prepared, and the experiment was carried out.

(1) JAK2 Gene Mutation

The JAK2-3 probe was intended to be synthesized with the nucleic acid sequence exhibited in Table 6. However, no probe was manufactured in order to proceed with the same after first confirming JAK2-1 and JAK2-2. In JAK2-1, a peak indicating a probe dimer appeared near 30° C., and JAK2-2 was selected without further proceeding (See FIG. 10).

(2) MPL Gene Mutation

For MPL, MLP-1 and MPL-2 did not distinguish W515L and W515K and had the same Tm value, and thus MLP-1 and MPL-2 were eliminated among the three candidates. Therefore, MPL-3 probe was selected (See FIG. 11). MPL-3 was prepared to fit on the opposite strand not to bind to MLP-1 or MPL-2. This can be used because the difference in Tm value due to change between TG>TT vs TG>AA is larger than the difference in Tm value due to change between CA>AA vs CA>TT.

(3) CALR Deletion Mutation

CALR-d1 was eliminated because poor melting peaks appeared in the DNA oligos corresponding to the wild type and deletion mutations. The CALR-d2 and CALR-d3 probes had the same sequence, but they were prepared to have different fluorescence types. The DNA oligo corresponding to the wild type and deletion mutants thereof had good Tm values and melting peaks. In actual samples, however, the peak corresponding to the mutation type (See red arrow in FIG. 12) was exhibited in the portion corresponding to the wild type due to the phenomenon in which the sequence collected by the probe repeatedly appeared in the target. Therefore, they were eliminated because it may be determined to include mutations in spite of wild type (See FIG. 12). FIG. 13 includes graphs illustrating melting point analysis using samples.

(4) CALR Insertion Mutation

The perfect matched target nucleic acid was considered to as a mutation type, and a non-perfect matched target nucleic acid was considered to as a wild type. These lead to easy detection of the insertion mutation. Thus, the insertion mutation was considered as the perfect matched target. CALR-in1, CALR-in2 and CALR-in3 showed low Tm values in the wild type, and thus the mutation type did not show any Tm value (red color of Homozygote in FIG. 14). CALR-in1 and CALR-in3 were prepared so that the used nucleic acid sequences were identical, but fluorescent materials only were different. Further, the CALR-in3 probe was prepared so that fluorescence bound to 5' to avoid interference with PNA probes detecting CALR-del52. CALR-in1 to CALR-in3 did not detect wild types, and thus CALR-in5p was used for gene mutation detection. The CALR-del52 mutation was recognized as a wild type in CALR-ins5, and thus the Tm value appears near 52° C. (See FIG. 7). However, it was known that incomplete match occurred at C of 3'-terminal, resulting in a slightly lower Tm than those of wild types.

Example 5

Optimal Combination of Selected Peptide Nucleic Acid Probes.

In order to find a combination that minimizes the interference phenomenon between the selected peptide nucleic acid probes, the configuration was prepared as the following table.

TABLE 6

|  | Mixed composition 1 | Mixed composition 2 |
|---|---|---|
| First solution (A set) | JAK2-2MPL-3CALR-d4CALR-in5p | JAK2-2CALR-d4 |
| Second solution (B set) | — | MPL-3CALR-in5p |

Probes which can result in interference phenomenon as described above were configured to be divided and separately present in solutions (mixed composition 2). Thus, it was confirmed that the problem of self-quenching was solved, and the mutation detection sensitivity increased (See FIGS. 15A and B).

Example 6

Setting of Detection Limit.

Six mutants and three wild types complementary thereto were artificially cloned and diluted to set the detection limit of the mixed composition 2 prepared above. Detection limits were set three times, and the setting was performed for each mutation of the causative genes.

The dilutions were performed in the dilution factor of 100% mutation, 50% mutation, 25% mutation, 10% mutation, 7.5% mutation, and 0% mutation. The results of the detection limit test confirmed that up to 10% mutation was detectable (See FIGS. 16A, B, and C).

Example 7

Verification of Sensitivity.

In order to verify the sensitivity of the mixed composition 2, FCMA was performed on the patient sample (total 57 patients) verified by Fragment analysis and Sanger sequencing, and it thus was confirmed that the abnormal curve was observed. The sensitivity was verified three times, and the verification was performed for each mutation of the causative genes (See Table. 7).

TABLE 7

| Gene | Mutation | Disease |
|---|---|---|
| JAK2 (n = 27) | V617F | PV (n = 20) |
|  | Additional exon 12 mutation | PV (n = 6), PMF (n = 1) |
| MPL (n = 6) | W515L/K | ET (n = 3) |
|  | W515L/K | PMF (n = 3) |
| CALR (n = 24) | Type 1 | ET (n = 9), PMF (n = 1) |
|  | Type 2 | ET (n = 8), PMF (n = 2) |
|  | Additional exon 9 mutation | ET (n = 4) |

As the experimental result, The JAK2 V617F mutation results were matched with allele specific real-time PCR results for all 27 samples.

MPL W515L/K mutation had 3 matches and 2 false negatives. However, the allele specific real-time PCR results showed less than 10% mutation, which was the detection limit or less. There was one sample with different Tm value from the existing set value. The nucleic acid sequence analysis revealed that the sample was MPL W515S.

The CALR type 1/2 mutations had 20 matches, 2 false positives and 2 false negatives. The false positive sample was an additional exon 9 mutation, which was confirmed to be a type 1 mutation as identified as a deletion including a region of the type 1 mutation probe position. The nucleic acid sequence analysis revealed that the false negative samples were 52 bp deletion and 4 bp deletion by c.1105_1156 del52 and c.1131_1151delinsGTGCCTCCTCCTGGAGG, respectively. As a result of fragment analysis, the difference in size of PCR product between the type 1 deletion (c.1092_1143del52) and the normal wild type was precisely matched, and thus this may be wrongly analyzed. It is expected to be confused because this was similar to the difference (5 bp) in size of PCR product between the type 2 insertion (c.1154_1155insTTGTC) and the normal wild type.

However, the nucleic acid sequence analysis revealed that they were not the CALR type 1 and typ2 mutations so that the present invention was determined to be superior to the fragment analysis (See Table 8 and FIGS. 17A and B).

TABLE 8

| Classification | Conventional test result | FMCA Test result |
| --- | --- | --- |
| CALR false positive | c.1092_1138del47 | Type 1 mutation (c.1092_1143del52) |
|  | c.1099_1132del34 | Type 1 mutation (c.1092_1143del52) |
| CALR false negative | Type 1 mutation (c.1092_1143del52): 52 bp difference | c.1105_1156del52: 52 bp difference (nucleic acid sequence confirmation) |
|  | Type 2 mutation (c.1154_1155insTTGTC): 5 bp difference | c.1131_1151delinsGTGCCTCCTCCTGGAGG: 4 bp difference (nucleic acid sequence confirmation) |

Therefore, the mixed composition 2 was used to verify the sensitivity of the FMCA test. The result revealed that the results of the real-time PCR and the fragment analysis test (the conventional test result) were consistent with each other in the samples having a detection limit of 10% or more.

Example 8

Verification of Specificity.

In order to verify the specificity of the mixed composition 2, FCMA was performed on 96 wild type DNAs. It was confirmed that no abnormal curves were observed (See FIG. 18). Specificity verification was performed three times, and the verification was performed for each mutation of the causative genes.

Example 9

Verification of Multiplex Detection.

It was confirmed that patient DNAs of the same causative gene were mixed to enable multiplex detection on the same channel (See FIG. 19). The multiplex detection verification was performed three times, and the multiplex detection verification was performed for each mutation of the causative genes. JAK2 V617F base substitution and other mutations were mixed and tested. MPL W515L and W515K mutation were mixed and tested. CALR type 1 and type 2 were mixed and tested. The experimental results are illustrated in FIG. 19.

It was also confirmed that patient DNAs of the different causative genes were mixed to enable multiplex detection on the different channels (See FIGS. 20A and 20B). The multiplex detection test was performed three times. Specifically, JAK2 V617F mutation and MPL W515L/K mutation were mixed and tested, JAKV V617F mutation and CALR type 1/2 were mixed and tested. MPL W515L/K mutation and CALR type 1/2 were mixed and tested.

It was confirmed that patient DNAs of 6 causative gene mutations were mixed, and 6 mutations were able to be detected at the same time (See FIGS. 21A, 21B and 21C). Multiplex detection verification was performed three times.

As described above, specific portions of the present invention are described in detailed. It will be apparent to those skilled in the art that these specific details are merely preferred embodiments and that the scope of the present invention is not limited thereby. It is therefore intended that the substantive scope of the present invention is defined by the claims appended hereto and their equivalents.

What is claimed is:

1. A kit for multiplex detection of a BCR/ABL negative myeloproliferative neoplasm-associated gene mutation, comprising
   a set of peptide nucleic acid (PNA) probes, wherein each probe consists of the sequences of
   SEQ ID NO: 7 binding to a mutation region of a Janus Tyrosine Kinase 2 (JAK2) gene;
   SEQ ID NO: 8 binding to a mutation region of a Mythroproliferative leukemia protein (MPL) gene;
   SEQ ID NO: 9 binding to a deletion region of a Calreticulin (CALR) Gene; and
   SEQ ID NO: 10 binding to an insertion region of the CALR Gene; respectively, wherein the peptide nucleic acid probe optionally contains a reporter molecule and a quencher molecule at each end of the probe, and
   a set of amplification forward and reverse primers comprising the sequences of SEQ ID NOS: 1 to 6, wherein each primer complementarily binds to a BCR/ABL negative myeloproliferative neoplasm-associated gene to specifically amplify a region of a mutation site, and wherein the BCR/ABL negative myeloproliferative neoplasm-associated gene mutation comprises one or more selected from the group consisting of (i) a substitution of valine at position 617 of the JAK2 gene with phenylalanine (JAK2 V617F), (ii) a substitution of tryptophan at position 515 of the MPL gene with leucine (MPL W515L), (iii) a substitution of tryptophan at position 515 of the MPL gene with lysine (MPL W515K), (iv) a substitution of tryptophan at position 515 of the MPL gene with arginine (MPL W515R), (v) a substitution of tryptophan at position 515 of the MPL gene with alanine (MPL W515A), (vi) a substitution of tryptophan at position 515 of the MPL gene with serine (MPL W515S), (vii) a c.1092_1143del52 base deletion of the CALR gene (L367fs*46) and (viii) a c.1154_1155insTTGTC base insertion of the CALR gene (K385fs*47).

2. The kit of claim 1, wherein the reporter molecule is any one selected from the group consisting of FAM (6-carboxyfluorescein), Texas red, HEX (2',4',5',7'-tetrachloro-6-carboxy-4,7-dichlorofluorescein), and Cy5.

3. The kit of claim 1, wherein the quencher molecule is any one selected from the group consisting of TAMRA (6-carboxytetramethyl-rhodamine), BHQ1, BHQ2, and Dabcyl.

4. A method for multiplex detection of a BCR/ABL negative myeloproliferative neoplasm-associated gene mutation, the method comprising:
- hybridizing a set of amplification forward and reverse primers comprising the sequences of SEQ ID NOS: 1 to 6, wherein each primer complementarily binds to a BCR/ABL negative myeloproliferative neoplasm-associated gene to specifically amplify a region of a mutation site, to a target DNA sample,
- amplifying a product obtained from the hybridizing step by PCR,
- adding a set of PNA probes to the amplified product, wherein each probe consists of the sequences of:
  - SEQ ID NO: 7 binding to a mutation region of a Janus Tyrosine Kinase 2 (JAK2) gene;
  - SEQ ID NO: 8 binding to a mutation region of a Myeloproliferative leukemia protein (MPL) gene;
  - SEQ ID NO: 9 binding to a deletion region of a Calreticulin (CALR) Gene; and
  - SEQ ID NO: 10 binding to an insertion region of the CALR Gene; respectively, wherein the peptide nucleic acid probe optionally contains a reporter molecule and a quencher molecule at each end of the probe,
- obtaining a melting curve; and
- comparing said melting curve with the standard melting temperatures of mutant genes,
- wherein the BCR/ABL negative myeloproliferative neoplasm-associated gene mutation comprises one or more selected from the group consisting of (i) a substitution of valine at position 617 of the JAK2 gene with phenylalanine (JAK2 V617F), (ii) a substitution of tryptophan at position 515 of the MPL gene with leucine (MPL W515L), (iii) a substitution of tryptophan at position 515 of the MPL gene with lysine (MPL W515K), (iv) a substitution of tryptophan at position 515 of the MPL gene with arginine (MPL W515R), (v) a substitution of tryptophan at position 515 of the MPL gene with alanine (MPL W515A), (vi) a substitution of tryptophan at position 515 of the MPL gene with serine (MPL W515S), (vii) a c.1092_1143del52 base deletion of the CALR gene (L367fs*46) and (viii) a c.1154_1155insTTGTC base insertion of the CALR gene (K385fs*47).

* * * * *

SEQUENCE LISTING

<160> NUMBER OF SEQ ID NOS: 30

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
agcagcaagt atgatgagca agc                           23

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
cagatgctct gagaaaggca tta                           23

<210> SEQ ID NO 3
<211> LENGTH: 21
<212> TYPE: DNA
<213> ORGANISM: Artificial Sequence

```
<220> FEATURE:
<223> OTHER INFORMATION: primer

<400> SEQUENCE: 3
gatctccttg gtgaccgctc t                                              21

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gggcggtacc tgtagtgtgc                                                20

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
gcagcagaga acaaatgaa gga                                             23

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
cctctctaca gctcgtcctt gg                                             22

<210> SEQ ID NO 7
<211> LENGTH: 14
<212> TYPE: DNA
<213> ORGANISM: Artificial Sequence
<220> FEATURE:
<223> OTHER INFORMATION: PNA probe

<400> SEQUENCE: 7
gtatgtgtct gtgg                                                      14

<210> SEQ ID NO 8
<211> LENGTH: 13
<212> TYPE: DNA
<213> ORGANISM: Artificial Sequence
<220> FEATURE:
<223> OTHER INFORMATION: PNA probe

<400> SEQUENCE: 8
ctgaggtggc agt                                                       13

<210> SEQ ID NO 9
<211> LENGTH: 15
<212> TYPE: DNA
<213> ORGANISM: Artificial Sequence
<220> FEATURE:
<223> OTHER INFORMATION: PNA probe

<400> SEQUENCE: 9
aagcctctgc tcctc                                                     15
```

-continued

```
<210> SEQ ID NO 10
<211> LENGTH: 15
<212> TYPE: DNA
<213> ORGANISM: Artificial Sequence
<220> FEATURE:
<223> OTHER INFORMATION: PNA probe

<400> SEQUENCE: 10
caattgtcct ctgcc                                                     15

<210> SEQ ID NO 11
<211> LENGTH: 21
<212> TYPE: DNA
<213> ORGANISM: Artificial Sequence
<220> FEATURE:
<223> OTHER INFORMATION: JAK2_PM

<400> SEQUENCE: 11
gtctccacag acacatactc c                                              21

<210> SEQ ID NO 12
<211> LENGTH: 21
<212> TYPE: DNA
<213> ORGANISM: Artificial Sequence
<220> FEATURE:
<223> OTHER INFORMATION: JAK2_1MM

<400> SEQUENCE: 12
gtctccacag aaacatactc c                                              21

<210> SEQ ID NO 13
<211> LENGTH: 21
<212> TYPE: DNA
<213> ORGANISM: Artificial Sequence
<220> FEATURE:
<223> OTHER INFORMATION: JAK2_2MM

<400> SEQUENCE: 13
gtctccacaa aaacatactc c                                              21

<210> SEQ ID NO 14
<211> LENGTH: 18
<212> TYPE: DNA
<213> ORGANISM: Artificial Sequence
<220> FEATURE:
<223> OTHER INFORMATION: PL-3_PM

<400> SEQUENCE: 14
tgctgaggtg gcagtttc                                                  18

<210> SEQ ID NO 15
<211> LENGTH: 18
<212> TYPE: DNA
<213> ORGANISM: Artificial Sequence
<220> FEATURE:
<223> OTHER INFORMATION: MPL-3_MM1

<400> SEQUENCE: 15
tgctgaggtt gcagtttc                                                  18

<210> SEQ ID NO 16
<211> LENGTH: 18
<212> TYPE: DNA
<213> ORGANISM: Artificial Sequence
<220> FEATURE:
<223> OTHER INFORMATION: MPL-3_MM2
```

```
<400> SEQUENCE: 16
tgctgaggaa gcagtttc                                                   18

<210> SEQ ID NO 17
<211> LENGTH: 19
<212> TYPE: DNA
<213> ORGANISM: Artificial Sequence
<220> FEATURE:
<223> OTHER INFORMATION: CALR-d4_PM

<400> SEQUENCE: 17
acgaggagca gaggcttaa                                                  19

<210> SEQ ID NO 18
<211> LENGTH: 18
<212> TYPE: DNA
<213> ORGANISM: Artificial Sequence
<220> FEATURE:
<223> OTHER INFORMATION: CALR-d4_MM

<400> SEQUENCE: 18
acgaggagca gaggacaa                                                   18

<210> SEQ ID NO 19
<211> LENGTH: 20
<212> TYPE: DNA
<213> ORGANISM: Artificial Sequence
<220> FEATURE:
<223> OTHER INFORMATION: CALR-ins5p_PM

<400> SEQUENCE: 19
ggaggcagag gacaattgtc                                                 20

<210> SEQ ID NO 20
<211> LENGTH: 20
<212> TYPE: DNA
<213> ORGANISM: Artificial Sequence
<220> FEATURE:
<223> OTHER INFORMATION: CALR-ins5p_MM1

<400> SEQUENCE: 20
ggaggcagag gacaaggagg                                                 20

<210> SEQ ID NO 21
<211> LENGTH: 22
<212> TYPE: DNA
<213> ORGANISM: Artificial Sequence
<220> FEATURE:
<223> OTHER INFORMATION: CALR-ins5p_MM2

<400> SEQUENCE: 21
cgaggagcag aggacaagga gg                                              22

<210> SEQ ID NO 22
<211> LENGTH: 167
<212> TYPE: DNA
<213> ORGANISM: Artificial Sequence
<220> FEATURE:
<223> OTHER INFORMATION: JAK2_WT

<400> SEQUENCE: 22
tctttctttg aagcagcaag tatgatgagc aagctttctc acaagcattt ggttttaaat     60
tatggagtat gtgtctgtgg agacgagagt aagtaaaact acaggctttc taatgccttt   120
ctcagagcat ctgttttgt ttatatagaa aattcagttt caggatc                  167
```

```
<210> SEQ ID NO 23
<211> LENGTH: 167
<212> TYPE: DNA
<213> ORGANISM: Artificial Sequence
<220> FEATURE:
<223> OTHER INFORMATION: JAK2_V617F1

<400> SEQUENCE: 23
tctttctttg aagcagcaag tatgatgagc aagctttctc acaagcattt ggttttaaat      60
tatggagtat gtttctgtgg agacgagagt aagtaaaact acaggctttc taatgccttt     120
ctcagagcat ctgttttgt ttatatagaa aattcagttt caggatc                    167

<210> SEQ ID NO 24
<211> LENGTH: 167
<212> TYPE: DNA
<213> ORGANISM: Artificial Sequence
<220> FEATURE:
<223> OTHER INFORMATION: JAK2_V617F2

<400> SEQUENCE: 24
tctttctttg aagcagcaag tatgatgagc aagctttctc acaagcattt ggttttaaat      60
tatggagtat gtttttgtgg agacgagagt aagtaaaact acaggctttc taatgccttt     120
ctcagagcat ctgttttgt ttatatagaa aattcagttt caggatc                    167

<210> SEQ ID NO 25
<211> LENGTH: 131
<212> TYPE: DNA
<213> ORGANISM: Artificial Sequence
<220> FEATURE:
<223> OTHER INFORMATION: MPL_WT

<400> SEQUENCE: 25
ccaccgccag tctcctgcct ggcgggggcg gtacctgtag tgtgcaggaa actgccacct      60
cagcagcagc aggcccagga cggcgctgag gcccagcact agatgcagag cggtcaccaa     120
ggagatccag g                                                          131

<210> SEQ ID NO 26
<211> LENGTH: 131
<212> TYPE: DNA
<213> ORGANISM: Artificial Sequence
<220> FEATURE:
<223> OTHER INFORMATION: MPL_W515L

<400> SEQUENCE: 26
ccaccgccag tctcctgcct ggcgggggcg gtacctgtag tgtgcaggaa actgcaacct      60
cagcagcagc aggcccagga cggcgctgag gcccagcact agatgcagag cggtcaccaa     120
ggagatccag g                                                          131

<210> SEQ ID NO 27
<211> LENGTH: 131
<212> TYPE: DNA
<213> ORGANISM: Artificial Sequence
<220> FEATURE:
<223> OTHER INFORMATION: MPL_W515K

<400> SEQUENCE: 27
ccaccgccag tctcctgcct ggcgggggcg gtacctgtag tgtgcaggaa actgcttcct      60
cagcagcagc aggcccagga cggcgctgag gcccagcact agatgcagag cggtcaccaa     120
ggagatccag g                                                          131
```

```
<210> SEQ ID NO 28
<211> LENGTH: 206
<212> TYPE: DNA
<213> ORGANISM: Artificial Sequence
<220> FEATURE:
<223> OTHER INFORMATION: CALR_WT

<400> SEQUENCE: 28
cctctctaca gctcgtcctt ggcctggccg gggacatctt cctcctcatc ttcctccttg    60
tcctcctcat cctcctcatc ctcatctttg tcctcatcat cctccttgtc ctctgcctcc   120
tcctcctctt tgcgtttctt gtcttcttcc tcctccttaa gcctctgctc ctcgtcctgt   180
ttgtccttca tttgtttctc tgctgc                                        206

<210> SEQ ID NO 29
<211> LENGTH: 154
<212> TYPE: DNA
<213> ORGANISM: Artificial Sequence
<220> FEATURE:
<223> OTHER INFORMATION: CALR_del52

<400> SEQUENCE: 29
cctctctaca gctcgtcctt ggcctggccg gggacatctt cctcctcatc ttcctccttg    60
tcctcctcat cctcctcatc ctcatctttg tcctcatcat cctccttgtc ctctgctcct   120
cgtcctgttt gtccttcatt tgtttctctg ctgc                               154

<210> SEQ ID NO 30
<211> LENGTH: 211
<212> TYPE: DNA
<213> ORGANISM: Artificial Sequence
<220> FEATURE:
<223> OTHER INFORMATION: CALR_ins5

<400> SEQUENCE: 30
cctctctaca gctcgtcctt ggcctggccg gggacatctt cctcctcatc ttcctccttg    60
tcctcctcat cctcctcatc ctcatctttg tcctcatcat cctccgacaa ttgtcctctg   120
cctcctcctc ctctttgcgt ttcttgtctt cttcctcctc cttaagcctc tgctcctcgt   180
cctgtttgtc cttcatttgt ttctctgctg c                                  211
```